(12) United States Patent
Froom

(10) Patent No.: US 9,031,734 B2
(45) Date of Patent: May 12, 2015

(54) SYSTEMS AND METHODS FOR NON-DESTRUCTIVE INSPECTION OF AIRPLANES

(75) Inventor: Douglas Allen Froom, Orangevale, CA (US)

(73) Assignee: Aerobotics, Inc., Wilmington, DE (US)

( * ) Notice: Subject to any disclaimer, the term of this patent is extended or adjusted under 35 U.S.C. 154(b) by 1 day.

(21) Appl. No.: 13/876,849

(22) PCT Filed: Sep. 26, 2011

(86) PCT No.: PCT/US2011/053190
§ 371 (c)(1),
(2), (4) Date: Mar. 28, 2013

(87) PCT Pub. No.: WO2012/050803
PCT Pub. Date: Apr. 19, 2012

(65) Prior Publication Data
US 2013/0261876 A1    Oct. 3, 2013

Related U.S. Application Data

(60) Provisional application No. 61/387,976, filed on Sep. 29, 2010, provisional application No. 61/387,980, filed on Sep. 29, 2010.

(51) Int. Cl.
*B64F 5/00* (2006.01)
*G01M 5/00* (2006.01)

(52) U.S. Cl.
CPC .................. *B64F 5/00* (2013.01); *B64F 5/0045* (2013.01); *G01M 5/0016* (2013.01); *G01M 5/0033* (2013.01); *G01M 5/0041* (2013.01); *G01M 5/0091* (2013.01); *Y10S 901/44* (2013.01)

(58) Field of Classification Search
USPC ................. 701/3, 29, 29.3, 30; 700/245, 248; 73/118.01, 118.03, 618, 619
See application file for complete search history.

(56) References Cited

U.S. PATENT DOCUMENTS

| 4,166,543 | A  | * | 9/1979  | Dahlstrom | .................... 700/251 |
| 6,220,099 | B1 | * | 4/2001  | Marti et al. | ...................... 73/633 |
| 6,637,266 | B1 | * | 10/2003 | Froom | .............................. 73/583 |

(Continued)

OTHER PUBLICATIONS

Douglas A Froom , PCT Application PCT/US2011/053190, Int'l Filing Date: Sep. 26, 2011, PCT Search Report dated May 3, 2012.

(Continued)

*Primary Examiner* — Mary Cheung
*Assistant Examiner* — Rodney Butler
(74) *Attorney, Agent, or Firm* — Ecotech Law Group, P.C.

(57) ABSTRACT

A method for managing an airplane fleet is described. The method includes: (i) developing a gold body database for an airplane model for each non-destructive inspection system implemented to detect defects; (ii) inspecting, over a period of time, a plurality of candidate airplanes of the airplane model, using different types of non-destructive inspection systems and the gold body database associated with each of the different types of non-destructive inspection systems, to identify defects present on the plurality of candidate airplanes; (iii) repairing or monitoring defects detected on the plurality of candidate airplanes; (iv) conducting a trend analysis by analyzing collective defect data obtained from inspecting of plurality of candidate airplanes; and (v) maintaining the airplane fleet, which includes plurality of candidate airplanes, by performing predictive analysis using results of trend analysis.

9 Claims, 23 Drawing Sheets

(56) References Cited

U.S. PATENT DOCUMENTS

| | | |
|---|---|---|
| 7,649,976 B2 | 1/2010 | Georgeson et al. |
| 2003/0089183 A1 | 5/2003 | Jacobsen |
| 2004/0176887 A1 | 9/2004 | Kent |
| 2008/0049889 A1* | 2/2008 | Tsukagoshi et al. ............... 378/4 |
| 2010/0235037 A1 | 9/2010 | Vian et al. |

OTHER PUBLICATIONS

Douglas A Froom , PCT Application PCT/US2011/053190, Int'l Filing Date: Sep. 26, 2011, IPER dated May 3, 2012.

Douglas A Froom , PCT Application PCT/US2011/053190, Int'l Filing Date: Sep. 26, 2011, Written Opinion dated May 3, 2012.

* cited by examiner

| SUMMARY OF DEFECTS FOUND IN HORIZONTAL STABILIZERS | | | | | | | | |
|---|---|---|---|---|---|---|---|---|
| NOUN | AFT BOX | | | | LEADING EDGE | | | |
| | LEFT | | RIGHT | | LEFT | | RIGHT | |
| SYSTEM | MX | MN | MX | MN | MX | MN | MX | MN |
| TYPE OF DEFECT | NUMBER OF DEFECTS FOUND BY REALTIME SYSTEM | | | | | | | |
| ADHESIVE CRACK | | | | | | | | |
| BLOWN CORE | | | | 2 | | | | |
| CELL CORROSION | 13 | 3 | 1 | 3 | 10 | 18 | 9 | 28 |
| CRACK | | | | | | | | |
| DAMAGED CORE | 2 | | 1 | | | | 1 | |
| FOM | | | | | | | | |
| MOISTURE | 24 | 26 | 14 | 36 | 26 | 96 | 43 | 38 |
| OTHER | | | 1 | | | | 1 | |
| SKIN CORROSION | | | | | 5 | 1 | 3 | |
| VOID | | | | 1 | | | | |
| NOT INSPECTED | | | | | | | | |

Trend Analysis of 50 Airplanes of an Airplane Fleet

| | PANEL DEFECT RATE | | | | | |
|---|---|---|---|---|---|---|
| | | PERCENT DEFECTIVE | | | | |
| NOMENCLATURE | PART ID LEFT, RIGHT | 10 AIRCRAFT | 20 AIRCRAFT | 30 AIRCRAFT | 40 AIRCRAFT | 50 AIRCRAFT |
| WING COMPONENTS | | | | | | |
| FLAP ASSEMBLY | 160, 1160 | 15.0 | 17.5 | 21.7 | 30.0 | 37.5 |
| AILERON ASSEMBLY | 170, 1170 | 100.0 | 87.5 | 85.0 | 85.0 | 83.7 |
| WING TIP ASSEMBLY | 190, 1190 | 20.0 | 27.5 | 33.3 | 43.8 | 51.0 |
| HORIZONTAL STABILIZER COMPONENTS | | | | | | |
| STABILATOR AFT BOX | 50, 1050 | 70.0 | 70.0 | 70.0 | 66.3 | 61.5 |
| STABILATOR OUTBOARD LEADING EDGE BOX | 60, 1060 | 85.0 | 80.0 | 76.7 | 75.0 | 74.0 |
| VERTICAL STABILIZER COMPONENTS | | | | | | |
| FORWARD BOX | 200, 1200 | 60.0 | 52.5 | 45.0 | 50.0 | 55.8 |
| TORQUE BOX | 210, 1210 | 30.0 | 27.5 | 33.3 | 30.0 | 29.8 |
| AFT LOWER BOX | 220, 1220 | 65.5 | 65.0 | 60.0 | 55.0 | 49.0 |

*Figure 22*

SYSTEMS AND METHODS FOR NON-DESTRUCTIVE INSPECTION OF AIRPLANES

RELATED APPLICATIONS

The present application claims priority from U.S. Provisional Applications having Ser. Nos. 61/387,980 and 61/387,976, both of which were filed on Sep. 29, 2010, which is incorporated herein by reference for all purposes.

FIELD OF THE INVENTION

The present invention relates to novel systems and methods for managing airplane fleets. More particularly, the present invention relates to managing airplane fleets using non-destructive inspection methods and predictive analysis.

BACKGROUND OF THE INVENTION

Frequent tragedies in airplane transportation have caused concern over the ability of airlines to evaluate the airworthiness of airplanes within their respective fleets. As airframes age, characteristics of materials, which make up airframe components, change due to stresses and strains associated with flights and landings. Moreover, there is a risk that a state of the airframe material may go beyond the point of elasticity (i.e., the point the material returns to its original condition) and extend into the point of plasticizing or worse, beyond plasticizing to failure. As a result, periodic inspections and testing are conducted on airplane components during the airplane component's life cycle. Such inspections and testing are mandated by governing bodies and are largely based on empirical evidence.

Inspections and testing of airplanes are bifurcated into two areas: destructive testing and nondestructive inspection (NDI), nondestructive testing (NDT) or nondestructive evaluation (NDE). "NDI," as this term is used hereinafter in the specification, encompasses the meanings conveyed by NDT and NDE, as those are described above. The area of destructive testing, as the name implies, requires the airplane component under scrutiny to be destroyed in order to determine the quality of that airplane component. This can result in a costly endeavor because an airplane component that may have passed the procedure is destroyed, and is no longer available for use. Frequently, where destructive testing is done on samples (e.g. coupons) and not on actual components, the destructive test may or may not be reflective of the forces that the actual component could or would withstand within the flight envelope of the airplane.

On the other hand, NDI has the obvious advantage of being directly applied to actual airplane components or sub-components in their actual environment. Several important methods of NDI that are performed in a laboratory setting are listed and summarized below.

Radiography involves inspection of a material by subjecting it to penetrating irradiation. Although effective damage detection has been done using neutron radiation, X-rays are the most familiar type of radiation used in this technique. Most materials used in airplane component manufacturing are readily acceptable to X-rays. In some instances, an opaque penetrant is needed to detect defects.

Real-time X-rays, which are frequently used as part of recent inspection techniques, permit viewing the area of scrutiny while doing a repair procedure. Some improvement in resolution has been achieved by using a stereovision technique where the X-rays are emitted from dual devices which are offset by about 15 degrees. When viewed together, these dual images give a three-dimensional view of the material. Still, the accuracy of X-rays is generally no better than plus or minus 10% void content. Neutrons (N-ray), however, can detect void contents in the plus or minus 1% range. The difficulty in implementing radiography raises safety concerns because a radiation source is being used. Nevertheless, in addition to detecting internal flaws in metals and composite structures using conventional non-radiography related methods, X-rays and neutrons are useful in detecting misalignment of honeycomb cores after curing, blown cores due to moisture intrusion, and corrosion.

Ultrasonic is the most common non-destructive inspection method for detecting flaws in composite materials. The method is performed by scanning the material with ultrasonic energy while monitoring the reflected energy for attenuation (diminishing) of the signal. The detection of the flaws is somewhat frequency-dependent and the frequency range and scanning method most often employed is called "C-scan." In this method, water is used as a coupling agent between the sending device and the sample. Therefore, the sample is either immersed in water or water is sprayed between the signal transmitter and the sample. This method is effective in detecting defects even in samples that are substantially thick, and may be used to provide a thickness profile. C-scan accuracies can be in the plus or minus 1% range for void content. A slightly modified method call L-scan can detect stiffness of the sample by using the wave speed, but requires that the sample density be known.

Acousto-ultrasonic, another non-destructive inspection method, is similar to ultrasound except that separate sensors are used to send the signal and other sensors are used to receive the signal. Both sensors are, however, located on the same side of the sample so a reflected signal is detected. This method is more quantitative and portable than standard ultrasound.

Acoustic emission, a yet another non-destructive inspection method, involves detecting sounds emitted by a sample that is subjected to stress. The stress can be mechanical, but need not be. In actual practice, in fact, thermal stresses are the most commonly employed. Quantitative interpretation is not yet possible except for well-documented and simple shapes (such as cylindrical pressure vessels).

Thermography (sometimes referred to as "IR thermography") is yet another non-destructive inspection method that detects differences in relative temperatures on the surface undergoing inspection. Differences in relative temperatures on the inspected surface are produced due to the presence of internal flaws. As a result, thermography is capable of identifying the location of those flaws. If the internal flaws are small or far removed from the surface, however, they may not be detected. In thermography, there are generally two modes of operation, i.e., an active and a passive mode of operation. In the active mode of operation, a sample is subjected to stress (usually mechanical and often vibrational) and the emitted heat is detected. In the passive mode of operation, the sample is externally heated and the resulting thermal gradients are detected.

Optical holography, a yet another non-destructive inspection method, uses laser photography to give three-dimensional pictures, which are called "holography." This method detects flaws in samples by employing a double-image method, according to which two pictures are taken while stress is induced on a sample between the times when a picture is taken. This method has had limited acceptance because of the need to isolate the camera and the sample from vibrations. However, it is believed that phase locking may eliminate this problem. The stresses that are imposed on the sample are usually thermal. If a microwave source of stress is used, moisture content of the sample can be detected. For composite material, this method is especially useful for detecting debonds in thick honeycomb and foam sandwich constructions. A related method is called shearography. In this method, a laser is used with the same double exposure technique as in holography where stress is applied between exposures. However, in this case an image-shearing camera is used in which signals from the two images are superimposed to provide an interference pattern and thereby reveal the strains in the samples. According to this method, strains are detected in a particular area, and the size of the pattern can give an indication of the stresses concentrated in that area. As a result, shearography allows a quantitative appraisal of the severity of the defect. The attribute of quantitative appraisal, relatively greater mobility of shearography over holography, and the ability to stress the sample using mechanical, thermal, and other techniques, has given this method wide acceptance since its introduction.

Unfortunately, current commercial industry inspection and repair methods suffer from several drawbacks. By way of example, the above described non-destructive inspection methods are largely limited to laboratory analysis. The current commercial industry inspection and repair methods are inefficient, costly and not standardized. As another example, these inspection and repair methods have seen little or no changes in the past 20 or 30 years and have not solved the "Aging Airplane" safety problems. As it stands now, inspection of airplane components are limited to the "Tap Test," visual inspection, and Eddy Current analysis. Furthermore, inspection timetables are developed and updated primarily as a function of anecdotal evidence, all too frequently based on airline catastrophes.

Despite a wealth of diagnostic tools mostly available in laboratory settings for detecting defects, what is, therefore, needed are novel systems and methods for effective airplane fleet management and that do not suffer from the above-described drawbacks encountered by the current airplane inspection methods and systems.

SUMMARY OF THE INVENTION

In view of the foregoing, in one aspect, the present invention provides systems and processes that use one or more NDI systems, which reveal different types of defects on the same components.

In another aspect, the present invention provides a method for managing an airplane fleet. The method includes: (i) developing a gold body database for an airplane model for each non-destructive inspection system implemented to detect defects; (ii) inspecting, over a period of time, a plurality of candidate airplanes of the airplane model, using different types of non-destructive inspection systems and the gold body database associated with each of the different types of non-destructive inspection systems, to identify defects present on the plurality of candidate airplanes; (iii) repairing or monitoring defects detected on the plurality of candidate airplanes; (iv) conducting a trend analysis by analyzing collective defect data obtained from inspecting of plurality of candidate airplanes; and (v) maintaining the airplane fleet, which includes plurality of candidate airplanes, by performing predictive analysis using results of trend analysis.

The construction and method of operation of the invention, however, together with additional objects and advantages thereof, will be best understood from the following descriptions of specific embodiments when read in connection with the accompanying figures.

BRIEF DESCRIPTION OF THE DRAWINGS

FIG. 22 shows an exemplar table resulting after conducting a trend analysis for defective components, which require repair or disassembly.

DETAILED DESCRIPTION OF THE PREFERRED EMBODIMENTS

Figure 1:
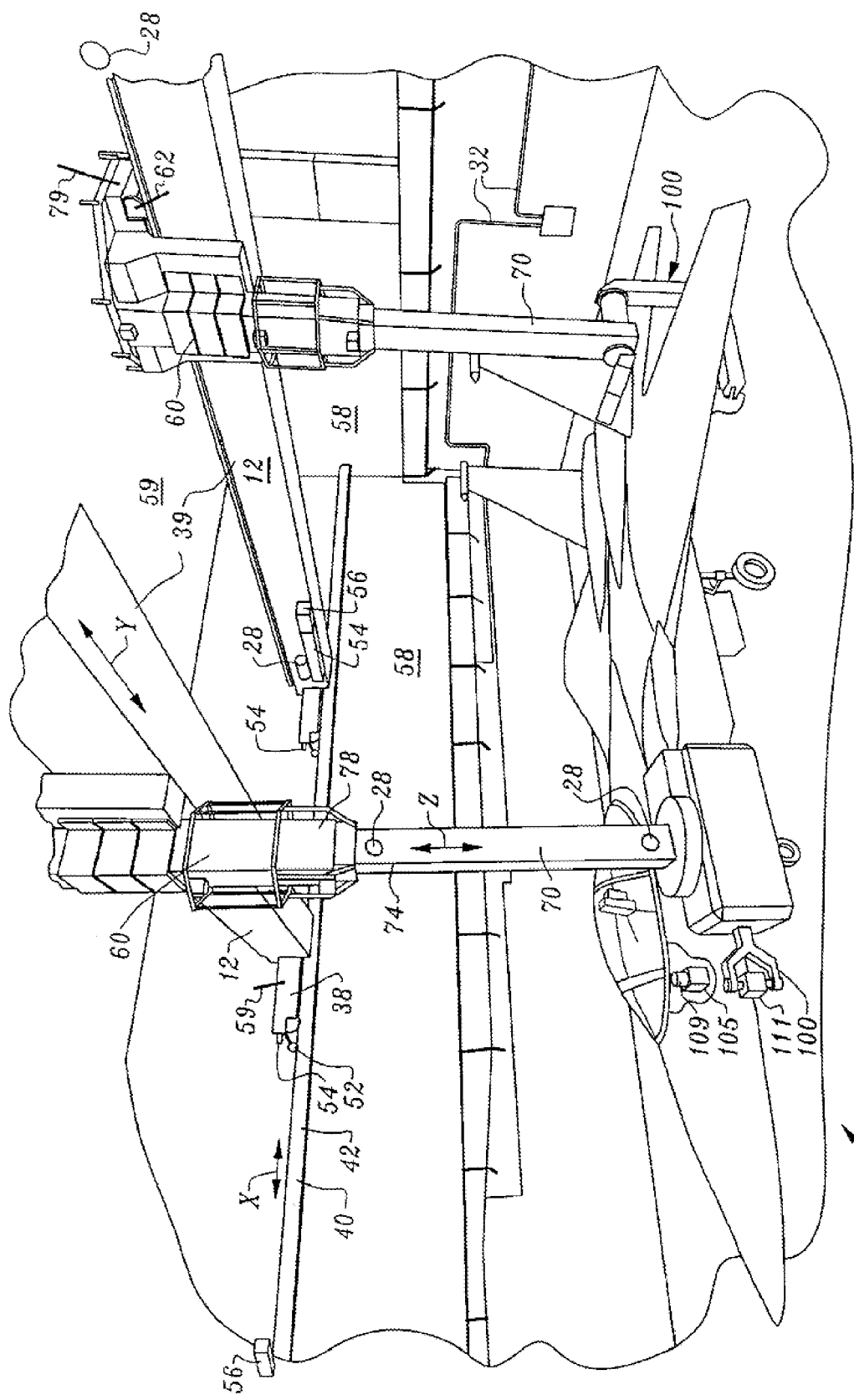
FIG. 1 is a perspective view inside a robotic envelope of some major components of a fleet management system, in accordance with one embodiment of the present invention.

In the following description, numerous specific details are set forth in order to provide a thorough understanding of the present invention. It will be apparent, however, to one skilled in the art that the present invention is practiced without limitation to some or all of these specific details. In other instances, well-known process steps have not been described in detail in order to not unnecessarily obscure the invention.

The present invention recognizes that currently, commercial safety integrity is continually compromised by not determining the extent of an airplane's structural defects. To this end, the present invention is directed to systems and processes that perform NDI of airplanes and components or sub-components thereof. Certain key aspects of the present invention involve systematic and automated inspection methods and apparatuses coupled with comparison to a gold body database (also known in the art as a "reference" or "standard") to allow for predictive analysis that is based on trend analysis of defects found in a plurality of candidate airplanes. A candidate airplane, as the term is used in this specification, refers to an airplane that undergoes inspection for defect detection. An airplane fleet includes a plurality of candidate airplanes.

NDI systems and methods of the present invention are contained inside or carried out in a structure, preferably configured as an enclosure. The structure includes walls, a ceiling, and a floor. A hangar door entrance is defined in a wall. Moreover, the structure utilizes concrete as shielding to attenuate the emission of radiation to the outside of the enclosure. In certain embodiments of the present invention, various safety measures may be implemented. By way of example, interlocks are provided to prevent the emission of radiation when personnel might be endangered because a door to a room, containing excessive amounts of radiation, is opened. Other measures, such as key controls and password authentication may be provided to prevent emission of radiation or other potentially hazardous activities, such as motion of robotic systems, without approval of authorized personnel. Radiation monitoring and alarm systems are preferably provided to detect abnormal radiation levels and provide warning.

For each NDI system or method implemented to detect defects, corbels are provided to support multiple robots. Walls, ceiling, and hanger door entrance are designed to support the corbels, permitting translation (e.g., along X-axis) across the items under inspection, testing or evaluation. Corbels designed to accommodate structural loading while maintaining accuracy and repeatability of robot position over six axes of movement, which are described below, within a narrow range of tolerances better than plus or minus about 0.250 inches, and preferably better than plus or minus about 0.120 inches. They accommodate structural loading of various types, e.g., floor loading, wind loading, loading in earthquake zones and loading from the mass of the robots.

In preferred embodiments, inventive NDI systems for inspecting an airplane component or sub-component include a beam arrangement for supporting and allowing translation of a carriage. The beam is mounted on rails which are attached to the corbels by the means of end trucks, providing movement along the length of the facility or X-axis. The carriage moves along the length of the beam providing movement in the Y-axis. A telescoping tube or mast is attached to the carriage in a vertical position, providing movement in the Z-axis. At the bottom of the mast, three axes of movement are provided, i.e., pitch, rotate, and yaw of the yoke to which the inspection apparatus is attached. The translations permit the system to scan an intact airplane to the component level or the sub-component level. The carriage is coupled to a mast structure for supporting and allowing translation of a yoke.

The mast comprises a plurality of tubes that can move telescopically to provide a large range of motion in a vertical direction, and at the same time, supporting large amounts of mass. In one embodiment of the invention, the beam arrangement is located overhead, for example, near the ceiling of the building. The building and beam arrangement form a gantry for supporting the carriage as well as the yoke which is mounted on the mast. In a preferred embodiment of the present invention, the yoke includes two members that may be extended telescopically to adjust the throat depth of the yoke.

In another embodiment of the present invention, the yoke is configured to accommodate surfaces that change a camber of the wing. In particular, configurations of the first member support a beam source and the second member supports an imaging device. In an alternative embodiment of the present invention, the mast supports a laser ultrasonic scanner. In this embodiment, a laser ultrasonic scanner is attached to the mast of the inspection and testing apparatus and configured with rotational axes to allow scanning in a plurality of directions across complex surfaces of the airplane, including its components or sub-components.

Real-time X-ray radiography is accomplished in motion utilizing multi-axis movement of robots to scan at a rate that is between about one and about three inches per second and at a magnification that is between about three times and about five times. Any pendulum or sway effect at the bottom of mast (with yoke attached) causes a real-time radiography image to unfocus, or in the alternative, get distorted and become unreadable to an operator. The problematic pendulum or sway effect is believed to be caused by two separate resonating frequencies, i.e., the fundamental frequency of the robot based upon the mass and rigidity of the robot structure, and the robot mounting to the housing facility which has its own resonating frequency when one ore more robots are in motion. Providing two separate parallel bridges mounted to single end trucks with carriage straddling both parallel bridges and the mast located between the two separate bridges yields acceptable results so long as the length of the bridge does not exceed a certain length, typically about 180 feet. Providing a single rail bridge typically permits a length of the bridge not to exceed about ninety-six feet.

Existing hangar structure may be modified or new facilities may be built to attenuate any pendulum effect and resonating frequencies that could distort robotic inspection readings. Facility modification or new design would be based upon three separate requirements, i.e., seismic, resonate frequency of the facility with one or more robots in motion, and the robotic envelope. Site surveys may determine the seismic activity, ground water location, type of soil, soil compaction and may result in building the facilities foundation as an isolation pad. The resonate frequency of the facility with the robots in a static position are modeled to evaluate the pendulum effect of the robots and to determine the amount of reinforcement of steel and concrete needed to meet frequency requirements for the facility's bearing walls. It is believed that as the robots move closer to the hangar door, the pendulum effects become unacceptable. Therefore, appropriate modifications may be made to the concrete hangar door header, and a lateral tie or footer may be provided at the ground level. Such modifications rigidify the side of the structure containing the hangar door to attenuate any resonate frequencies to acceptable levels during the airplane inspection using robots. The robotic envelope is determined based on the type of airplane that is subject to inspection within the facility. The envelope is factored in, and any resonate frequencies are attenuated in order to provide inspection accuracy and repeatability.

Inspection of airplane wings requires the control surfaces to be extended to allow for a total wing inspection. This wing configuration causes sharp radial surface turns at the fore and aft ends of the wings' leading and trailing edge surfaces and the inability for a normal "C"-shaped yoke to conform to these areas to perform a total inspection of the part. The solution to this problem is to provide a modified C-shaped yoke with a lower arm having an articulating member, akin to a double joint, in order to allow the lower arm to tuck underneath the control surface.

When the preliminary designs of the buildings, robots, and end effectors are completed, modeling of the entire system may be performed to assure accuracy and repeatability of robot positioning. Oscillatory excitation of the system components resulting from robot motion and acceleration and deceleration may be analyzed. Designs of the system components may be modified to maximize desirable characteristics, such as accuracy and repeatability of robot positioning, while minimizing undesirable characteristics, such as unwanted oscillatory excitation of system components.

Figures 1A, 2A:
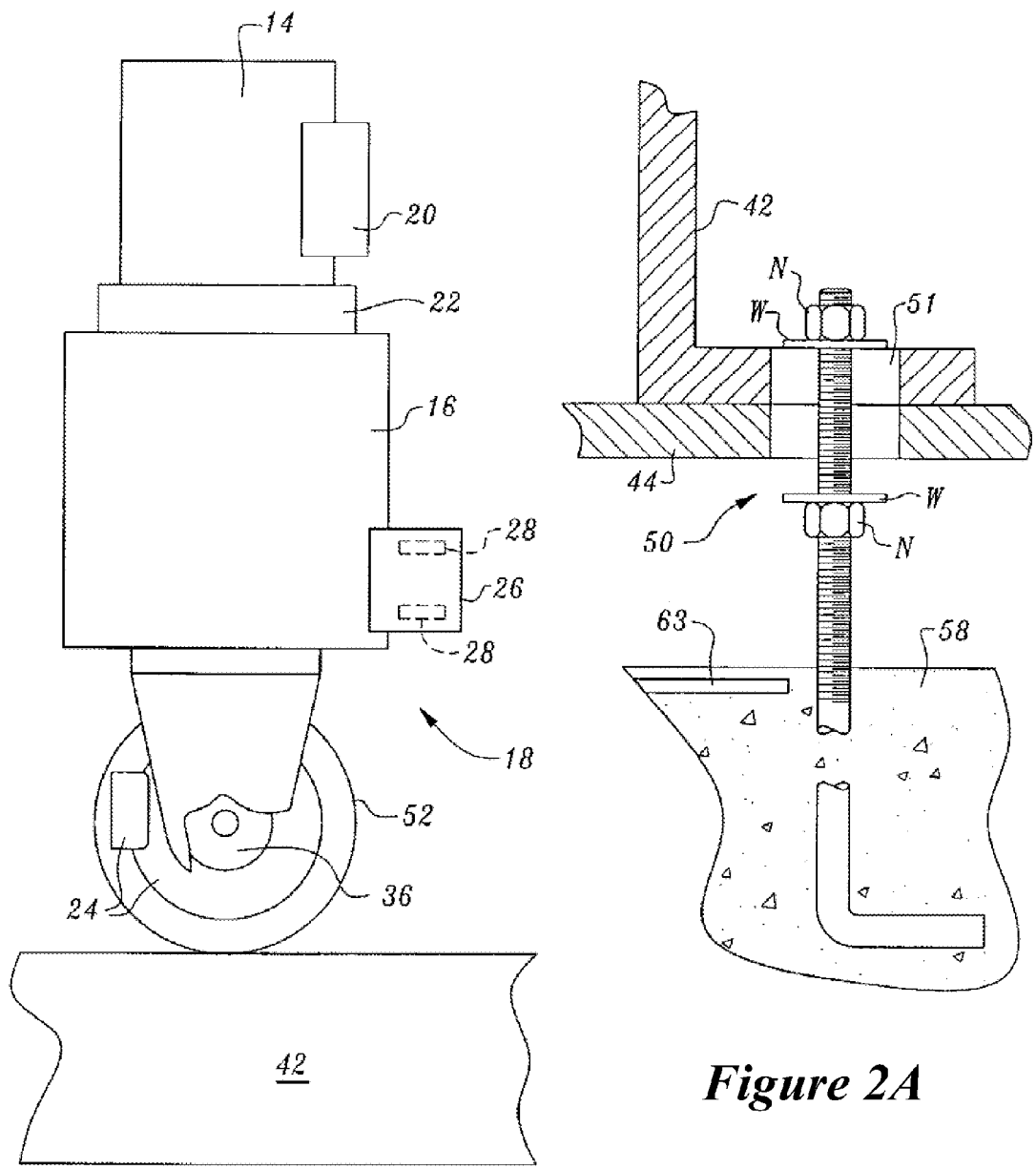
FIG. 1A shows one robotic movement system, in accordance with one embodiment of the present invention, through the X-axis.
FIG. 2A shows an attachment, in accordance with preferred embodiments of the present invention, to a rail in the X-axis as shown in FIG. 1A.

FIGS. 1-13 described below show various systems and sub-systems used in certain embodiments of the present invention, to implement, among other things, the methods of the present invention. A Robotic Overhead Positioner (ROP), (e.g., as shown in FIG. 1) is a gantry robot that resembles an overhead crane. The ROP allows movement in three linear directions (i.e., X, Y, and Z) and three rotational directions (i.e., Yaw, Pitch and Roll described below). Generally, to move in each of these directions, it uses a variable-speed DC motor 14 (which is shown in greater detail in FIG. 1A), a gearbox 16, and an encoder 22 including a drive mechanism 18 having wheels 52. Power to turn the motor (thus moving the robot) is supplied by a controller 20. Each motor 14 includes encoder 22, which instructs controller 20 regarding distance of travel. Motor 14 also includes a solenoid energized electric disc brake 24, which keeps the robot in a frozen position whenever controller 20 is not supplying power to motor 14. For each direction robot 12 is capable of moving, there is also an absolute-positioning resolver 26, which instructs controller 20 regarding the robot's location via encoder 22. Limit switches 28 inside resolver 26 prevent the motor 14 from driving wheeled drive mechanism 18 beyond its end of travel. Power to motor 14 and signals to controller 20 are supplied via cables 32 (as shown in FIG. 1), which are fully insulated and which have military-standard connectors. As shown in FIG. 1A, heavy-duty frictionless bearings 36 are used throughout, in accordance with one embodiment of the present invention, to maximize system reliability.

Figure 2:
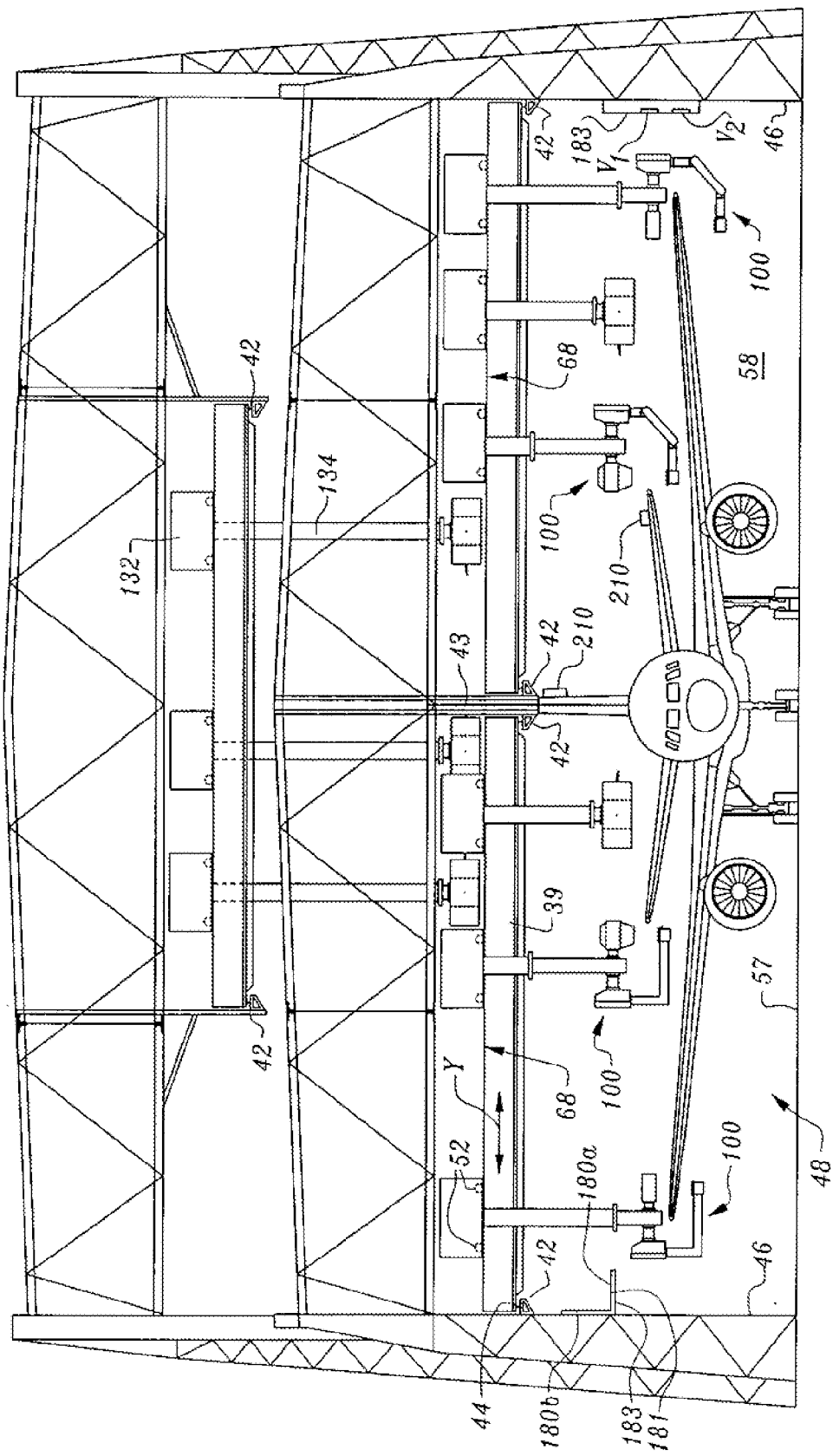
FIG. 2 is a front view of a fleet management system, in accordance with preferred embodiments of the present invention, for managing a commercial airplane fleet.

As shown in FIGS. 1 and 1A, a bridge 38 moves in a first linear direction (i.e., X-axis) on a runway 40. Runway 40 is made of sets of two parallel rails 42 (shown in FIG. 2) mounted on rail ledges 44 (shown in FIG. 2A). FIG. 2 shows one rail 42 on each sidewall 46 (and two rails 42 on a central corbel 43) of the inspection bay 48. Rails 42 have adjusters 50 for leveling and parallel alignment, as shown in FIG. 2A.

Wheels 52, as shown in FIGS. 1A and 2, are designed to support bridge end trucks 38. A pair of wheels 52 rides on rails 42. Each pair of wheels has its own motor 14 and its own resolver 26. Bridge 38 encloses and supports drive mechanism 18. As motor 14 turns, wheels 52 turn, moving bridge 38 back and forth on the rails 42. The dual motor 14/resolver 26 scheme enables controller 20 to avoid bridge 38 skewing off the rail 42. If limit switches 28 in the resolver 26 were to fail, thereby allowing an operator to move bridge 38 to the very end of the rails 42, shock absorbers 54 on bridge 38 and end-stops 56 on rails 42 prevent bridge 38 from striking walls 58. A crank 59 is provided on each end of bridge 38 as a manual backup motion system to allow the bridge to move without motor 14.

Figure 3:
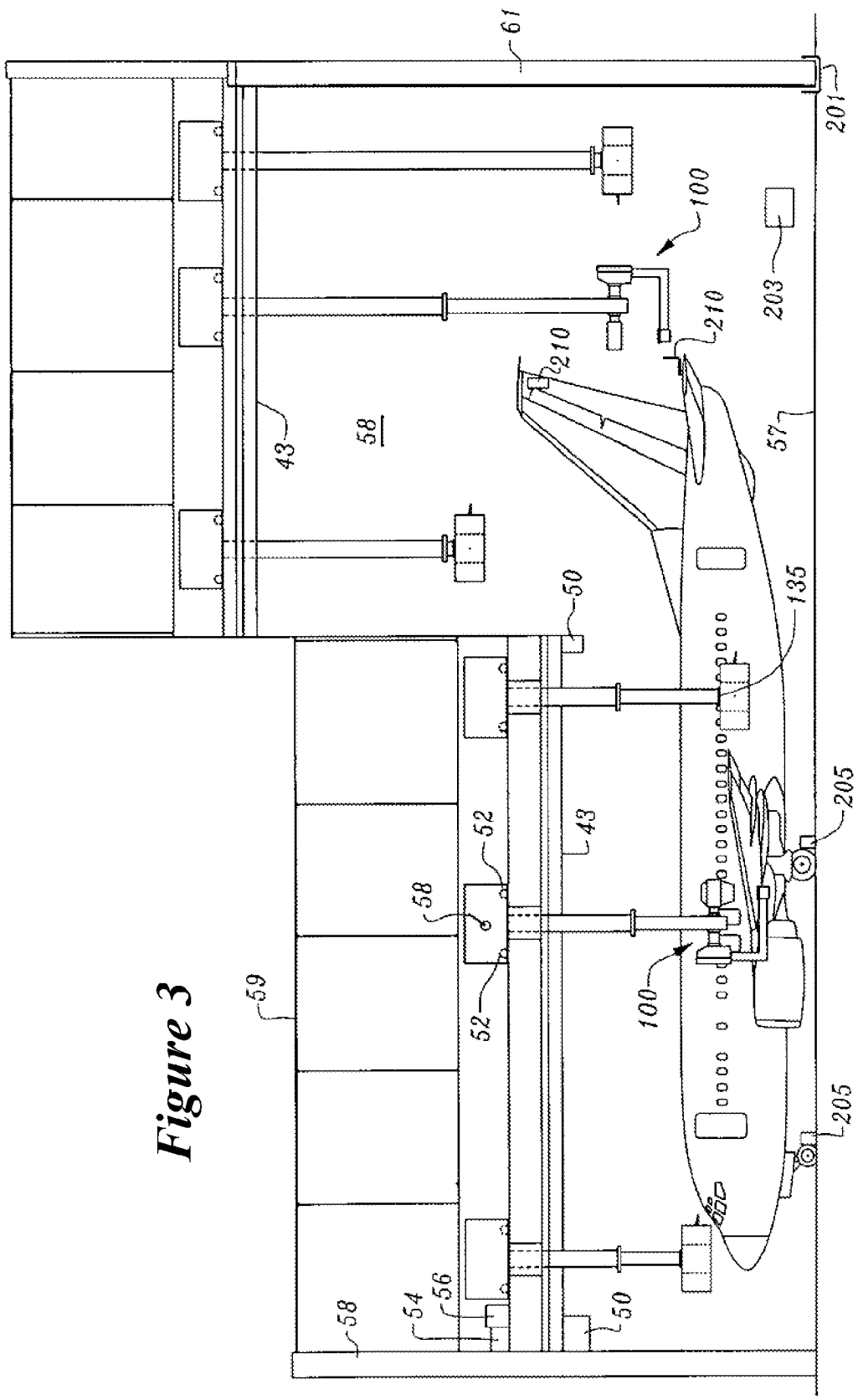
FIG. 3 is a side view of a commercial airplane fleet management system shown in FIG. 2.
Figure 3A:
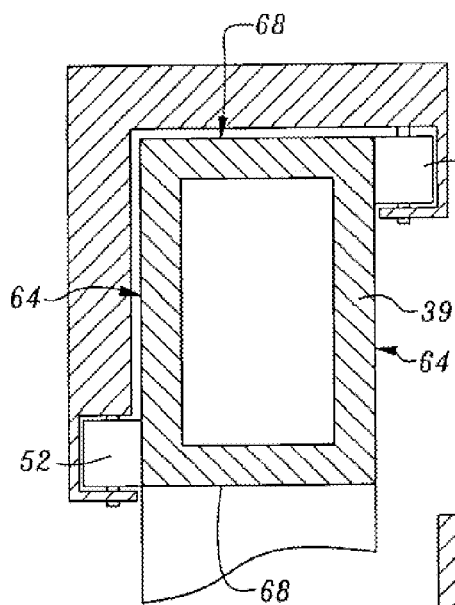
FIG. 3A shows a vertical mast support, in accordance with preferred embodiments of the present invention.

FIGS. 1 and 2 show the second linear direction (i.e., Y-axis) where a trolley 60 moves along a span 39 which extends between two rails 42. Similar to X-axis, trolley 60 moves along span 39 in a dependent relationship, as shown in FIG. 3A. Span 39 is box-shaped and has spaced parallel vertical rails 64 and spaced parallel horizontal rails 68 forming an enclosed box. The weight of trolley 60 is bearing on its wheels 52 that ride on opposed outer faces of each vertical rail 64. As motor 14 turns, wheels 52 also turn, moving trolley 60 left and right (along Y-axis) on span 39. One wheel set 52 rides on a lower edge of one vertical rail 64 and another wheel set 52 rides on a top edge of opposite vertical rail 64 to keep trolley 60 (and thus the mast 70) from tilting. Span 39 preferably has an upwardly projecting central crown 68 (as shown in FIG. 2) of about one-half inch when unloaded and bows one-half inch downwardly when trolley 60 moves to the middle of span 39. Thus, span 39 is, therefore, normalized (i.e., level) along a length. If limit switches 28 in resolver 26 were to fail, allowing an operator to move trolley 60 to the end of rails 42, shock absorbers 54 on span 39 and end-stops 56 on the span's ends prevent trolley 60 from striking walls 58. A crank 62 is provided on each trolley 60 as a manual backup system to allow reorientation of trolley 60 along span 39. The trolley's drive is similar to that shown in FIG. 1A.

Figure 4A:
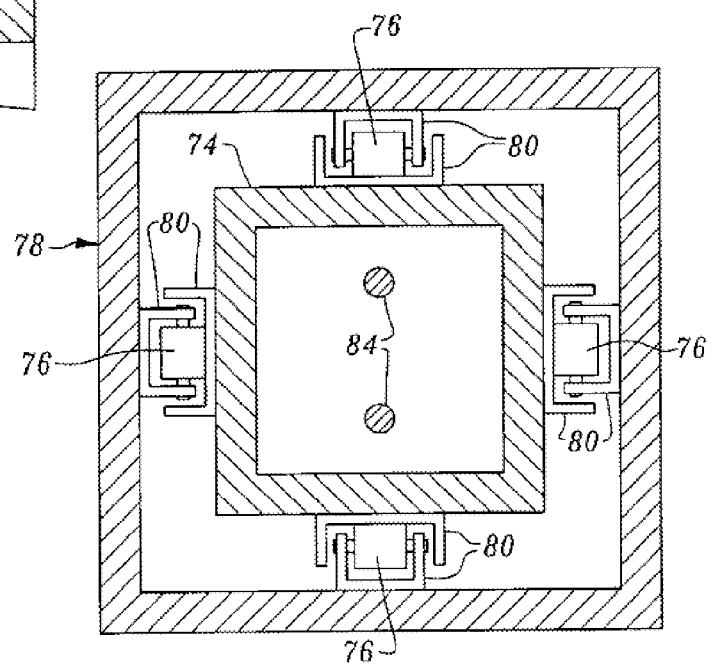
FIG. 4A shows a section of the mast, in accordance with preferred embodiments of the present invention.
Figure 5A:
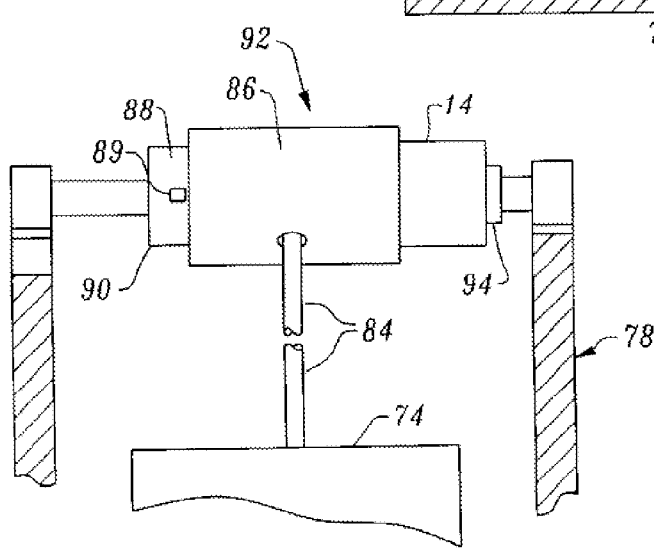
FIG. 5A shows some major components of a mast drive system, in accordance with preferred embodiments of the present invention.
Figure 4:
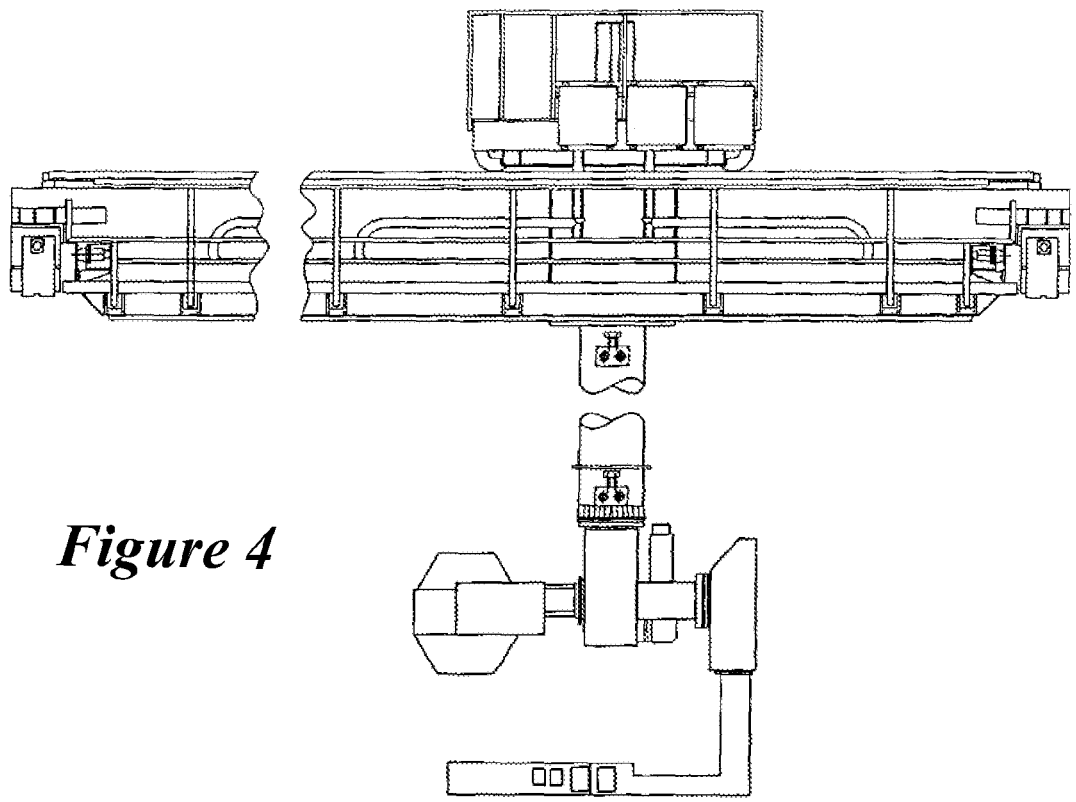
FIG. 4 is a side view of an N-ray system, in accordance with preferred embodiments of the present invention.
Figure 5:
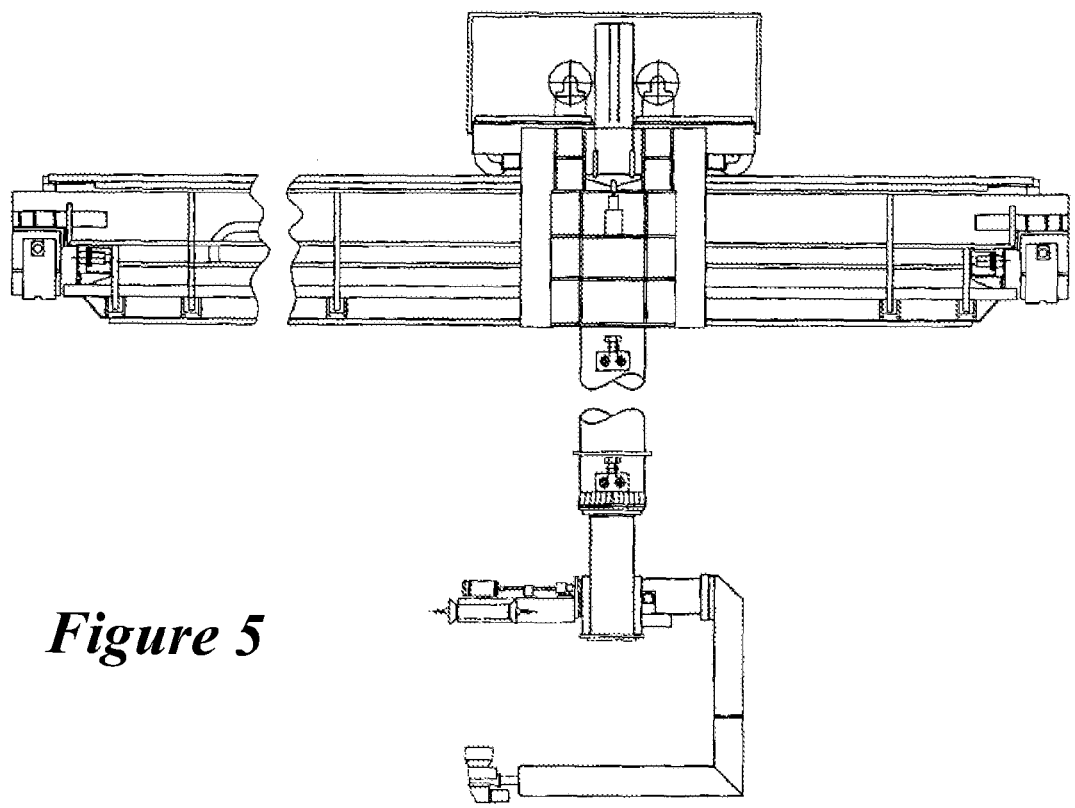
FIG. 5 is a side view of an X-ray system, in accordance with preferred embodiments of the present invention.
Figure 6:
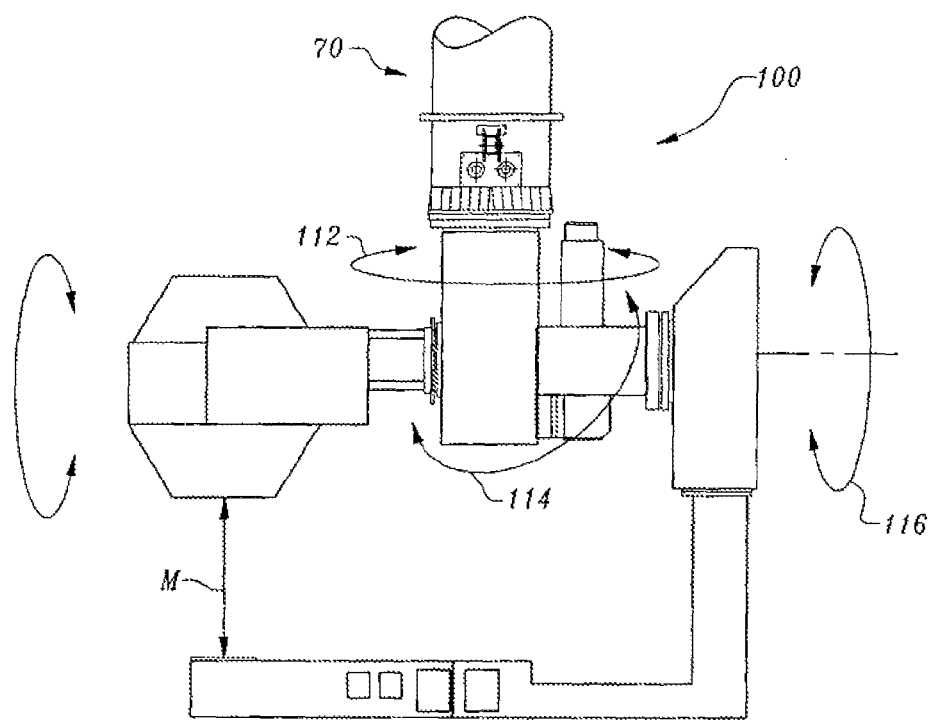
FIG. 6 is a side view of an N-ray yoke, in accordance with one embodiment of the present invention.

The third linear direction (i.e., Z-axis) moves mast 70 on trolley 60 up and down via positioner 92, which is shown in FIG. 5A. Mast 70 is preferably capable of hoisting at least 5000 pounds, and is designed such that the failure of any single part of the system will not cause its sensor array, located at the free end of mast 70, to fall to the bottom of mast travel. Mast 70 is a box-shaped inner telescoping tube 74 with wheels 76 on an inner surface of box-shaped outer tube 78 riding on rails 80 as shown in FIG. 4A. Mast 70 is hoisted by dual cables 84 (shown in FIGS. 4A and 5A) and has two drums 86 (only one is shown to simplify illustration). As motor 14 turns, each drum 86 deploys a cable 84, hoisting inner tube 74. Each drum 86 has a brake 88 mounted to its drive shaft 89 to prevent tube 74 from falling if one brake 88 should fail. A load sensing mechanism 90 embodied as an overload clutch is provided on hoisting system brake 88 to stop the mast if a sensor supporting yoke 100 (e.g., as shown in FIG. 2) should catch on an object, as it is hoisted up or down or if there is a system overload. This load sensing mechanism 90 will also stop positioner 92 when one component of the hoist system quits operating. For a backup system, each cable/drum system is capable of hoisting the mast at full load. If the hoist were to over-speed, another sensor 94, monitoring amperage would again perform to trigger an emergency stop. A crank 79 of FIG. 1 is provided on each mast 70 as a manual backup motion system.

Figure 7:
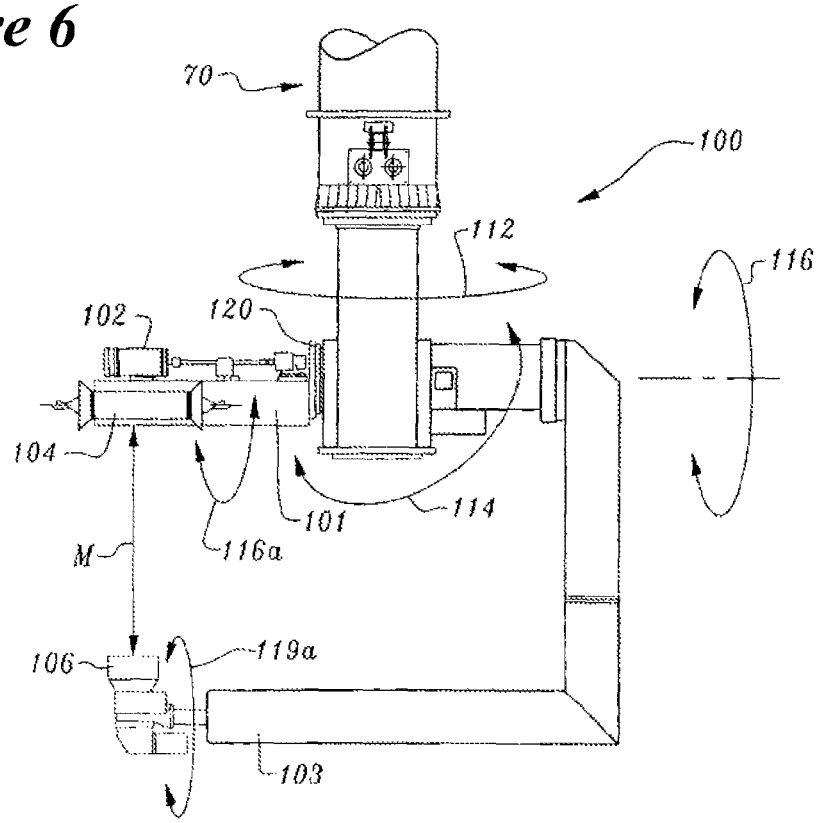
FIG. 7 is a side view of an X-ray yoke, in accordance with one embodiment of the present invention.
Figure 8:
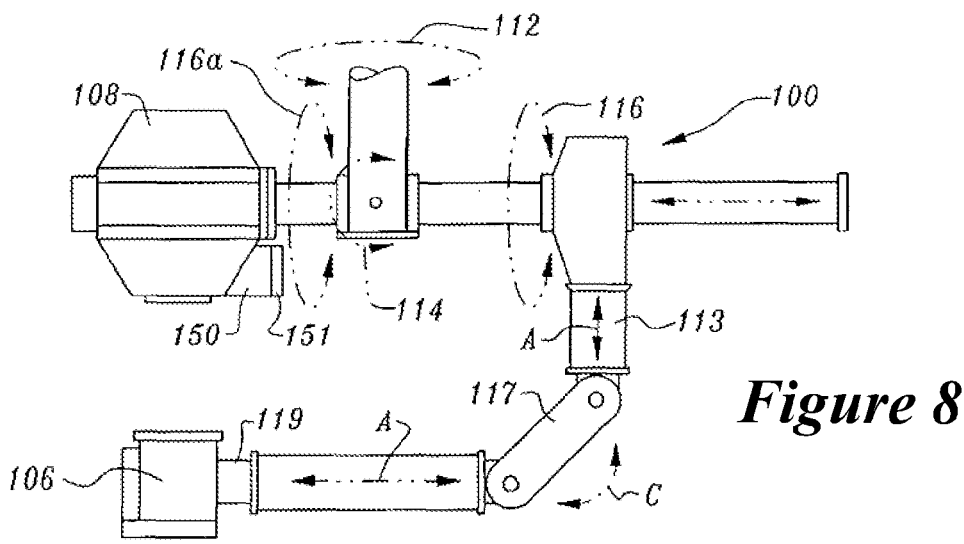
FIG. 8 is a side view of an adjustable lower leg of an N-ray yoke, in accordance with preferred embodiments of the present invention.
Figure 9:
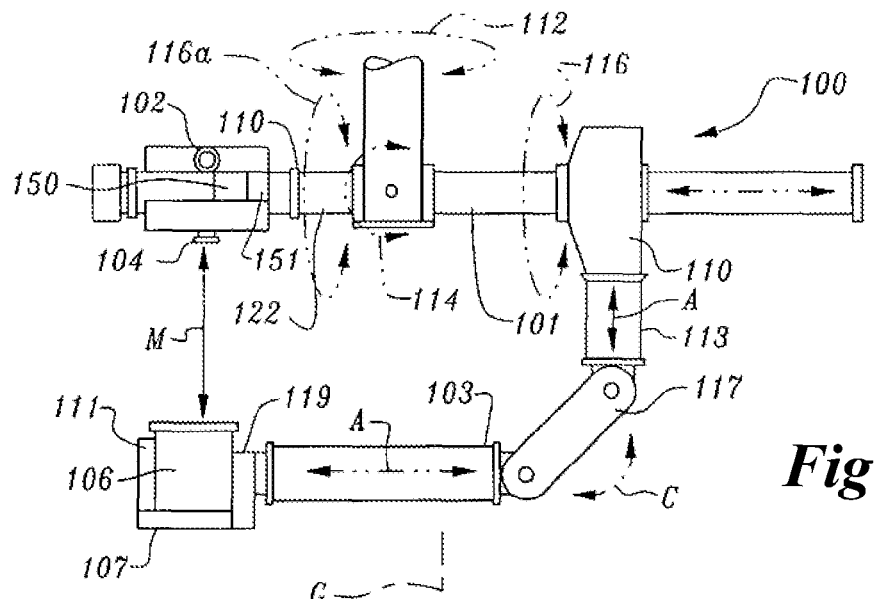
FIG. 9 is a side view of an adjustable lower leg of an X-ray yoke, in accordance with preferred embodiments of the present invention.

Three rotational axes are incorporated into each inspection yoke 100, as shown in FIGS. 6 through 9. Yoke 100, as mentioned before, is a C-shaped structure with an adjustable mouth "M" which spans the gap between the sources and receiver. Two X-ray sources 102, 104 (as shown in FIGS. 7 and 9), having differing outputs are mounted on top support 101 of yoke 100 and an image receiver 106 is mounted on the bottom by arm 103. Yoke 100 may also support a collision-avoidance paneling 110. The paneling is a pressure sensitive sheath and is mounted on all lower extremities of mast 70. The pressure sensitive paneling prevents gross contact with the airplane by mandating a stop signal in the presence of a triggering pressure. During the scanning of the airplane surfaces, the surface (e.g., wing) is positioned between X-ray sources 102 and 104 and N-ray source 108 (shown in FIGS. 6 and 8) and imager 106. A film source 107 may supplement or supplant imager 106.

A first rotational axis 112 (i.e., Yaw) rotates inspection yoke 100 in a horizontal plane at the bottom of mast 70. A second rotational axis 114 (i.e., Pitch) pivots inspection yoke 100 in a vertical plane at the bottom of mast 70. A third rotational axis 116 (i.e., Roll) rotates inspection yoke 100 in a plane at the end of the pitch axis; this plane is oriented perpendicular to the pitch axis. It is noteworthy that X-ray sources 102 and 104, and N-ray source 108 are independently rotatable about 116*a*. Further, each arm (e.g., bottom arm 103 or a side arm) may change in length as shown by double ended arrows "A" as shown in FIGS. 8 and 9. A link 117 connecting bottom and side arms 103, 113 can rotate about curved arrow "C" to adjust the dimension of adjustable mouth "M," in conjunction with the telescoping arm's length along arrow "A."

X-ray sources 102 and 104 are mounted on a movable support such that only one of the two sources may be aimed at imager 106 during an imaging event by rotation about 116*a*. This support, called a turret 120 (shown in FIG. 7), is rotated 90 degrees by a stepper motor 122 (shown schematically in FIG. 9). Only the X-ray source aimed at imager 106 may be activated unless a permanent record is desired via a film source 107 which rotates in the place of imager 106. Alternatively, the film source 107 can rotate about axis 119 (denoted by arrow 119*a* in FIG. 7) to orient the film source 107 to X-ray source 102 and 104. X-ray sources 102 and 104 are indexed into position as a function of the object being scanned, its thickness, and its composition (e.g., composition versus metal). Imager 106 is an image intensifier, which directs the X-ray image to the control room operator CRT screen. A bottom arm 103 may also carry another type of X-ray imaging system 111 for backscatter X-ray (reverse geometry X-ray). A sender unit 111 is shown mounted adjacent imager 106. Photo-multiplier tubes 109 (shown in FIG. 1) are positioned inside the airplane to receive digital images from sender 111. Receivers 105 are also placed on the inside of the production airplane structures and direct digital imaging information to be sent to the control room operators. Yoke manipulative and imaging capabilities specified for either the N-ray or X-ray could be incorporated in the other.

Because of the varying change in the thickness of airplane internal structures (such as wings), the X-ray source output (KVP Kilovoltage Penetrating Power, MA Milliamps Current) is preferably controlled by robotic coordinates to allow ramp up or ramp down of X-ray penetrating power. This allows clear and precise imaging. It also allows an operator to focus attention to the viewed images and not constantly adjusting output due to the change in the airplane structure material thickness. More importantly, each and every airplane is inspected based on the same settings, conditions and a relevant gold body database.

Yoke 100 also contains a heat gun 150, somewhat like a hair dryer. This is used on both the X-ray and N-ray yokes to allow an operator to verify and distinguish the presence of moisture, water or fuel inside the aluminum or composite bonded structure. Current industry NDI methods and systems cannot distinguish the difference between moisture and sealant. Once a defect area is detected by either an X-ray or N-ray inspection system or method, heat is applied by the yoke's heat gun 150 to that specific area. Heat out generation is monitored by an infrared pyrometer 151 in order not to exceed a limit, preferably 160 degrees Fahrenheit, on the structure where the heat is applied. If moisture is present, the applied heat causes migration of the fluid away from the heat source due to expansion of the air within the heated structure area. Heat images are taken before and after heating. Alternate "before and after" images flash on the operator's CRT screen and image picture subtraction is accomplished. The difference allows the operator to watch moisture migration. This procedure is important in locating water entry paths within the airplane structure or component.

Figure 10:
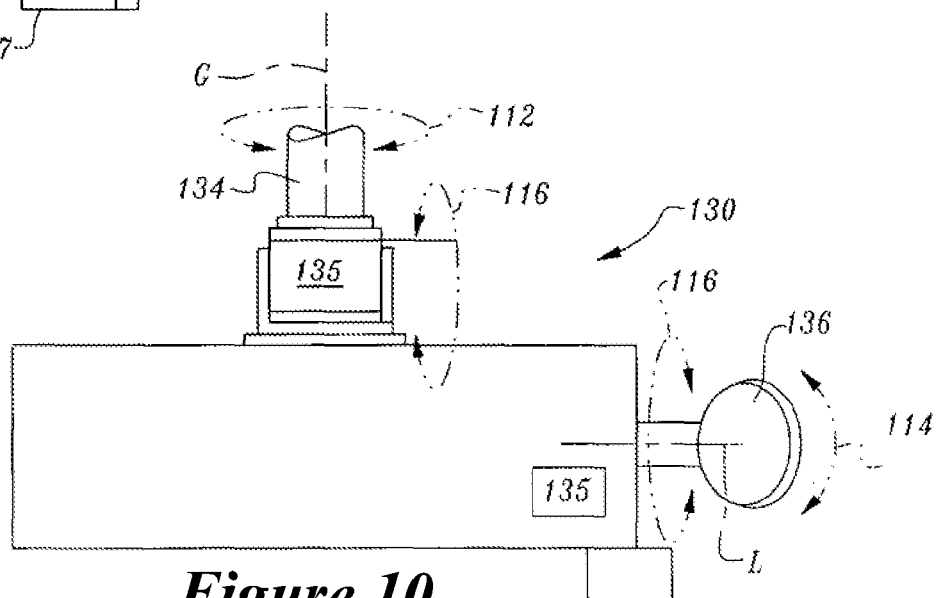
FIG. 10 is a side view of pitch, rotate and yaw of a laser yoke, in accordance with preferred embodiments of the present invention.
Figure 11:
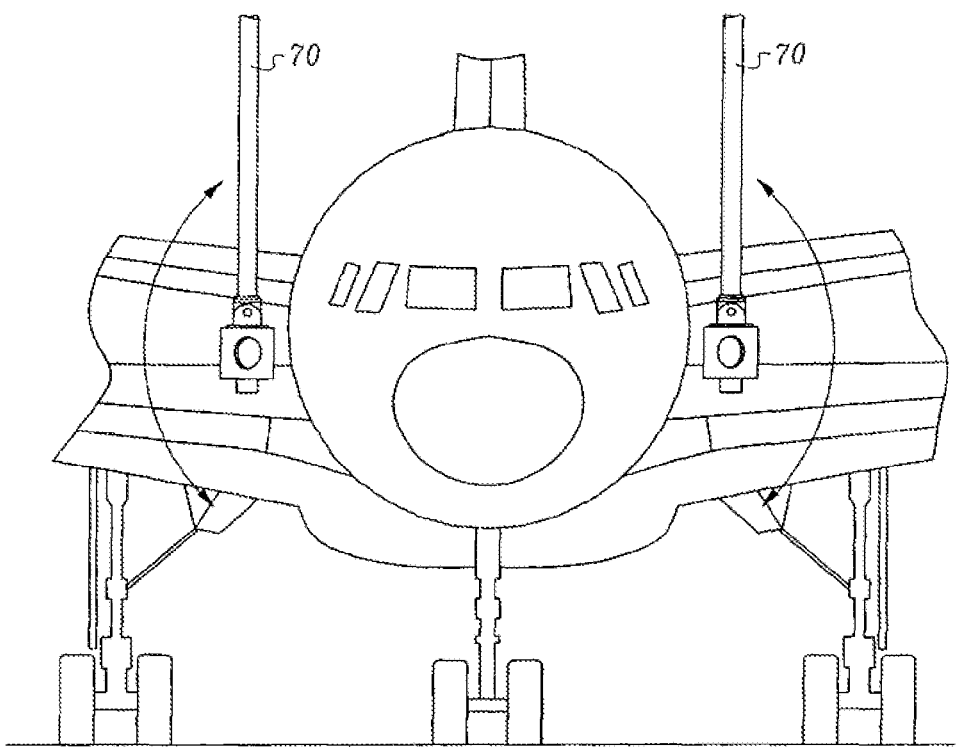
FIG. 11 is a front view of a laser addressing the airplane, in accordance with preferred embodiments of the present invention.
Figure 12:
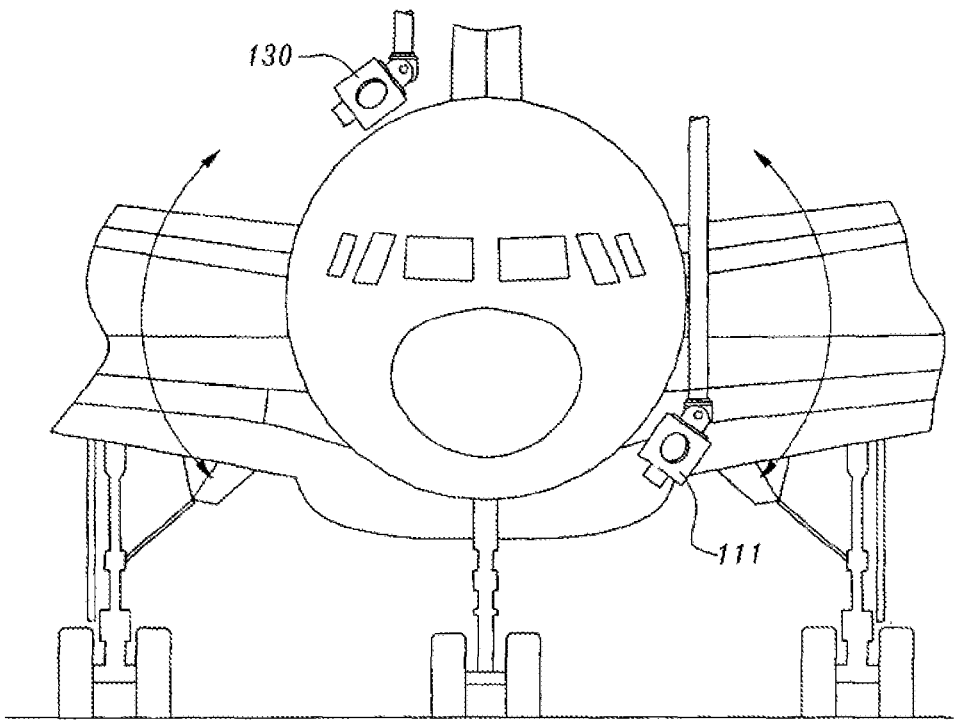
FIG. 12 is a front view of a laser addressing an airplane and the configuration of the laser and the airplane is shown in accordance with preferred embodiments of the present invention.
Figure 13:
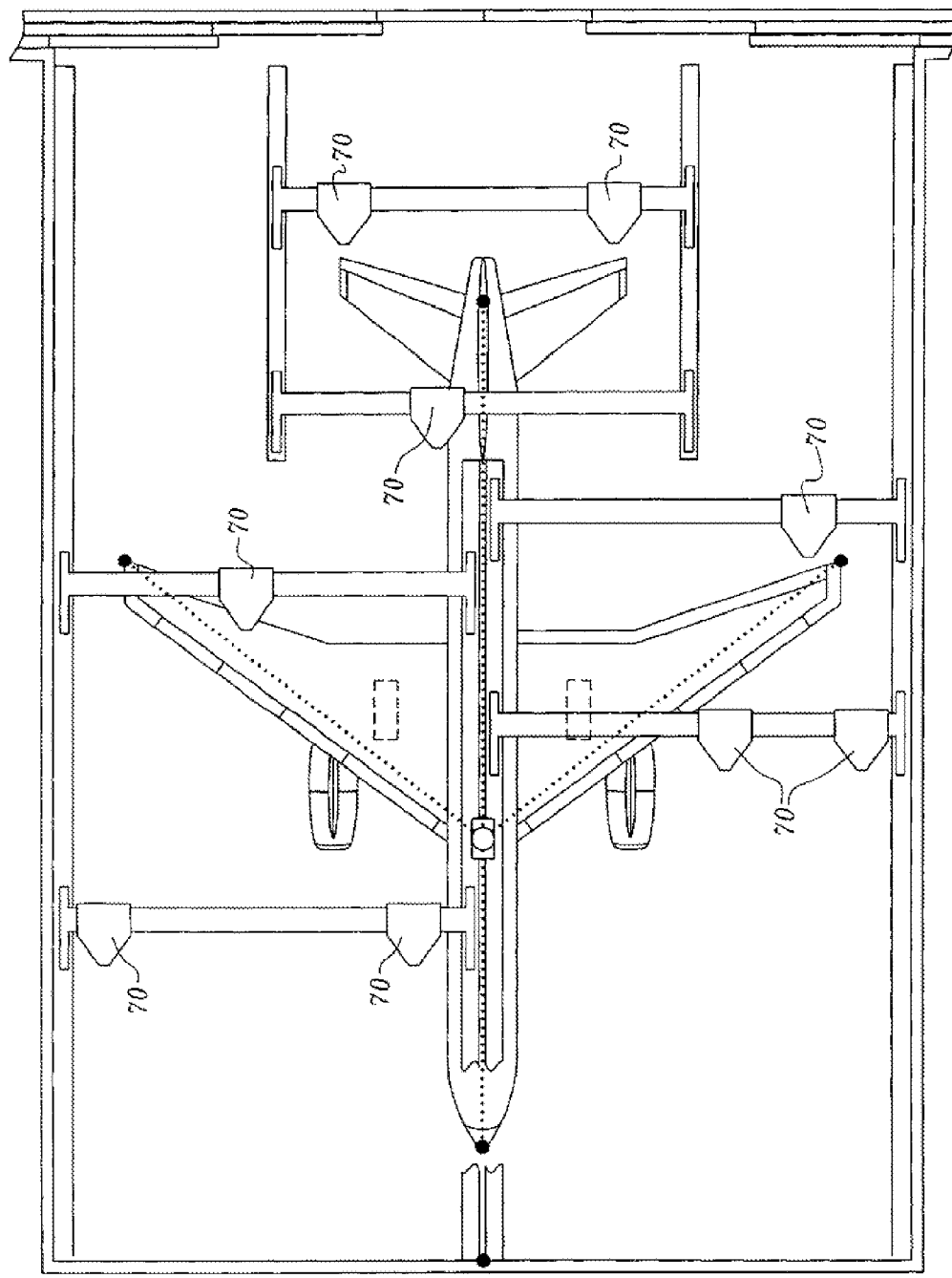
FIG. 13 is a top view of a fleet management system, in accordance with preferred embodiments of the present invention.

A laser ultrasonics ("laser UT") apparatus, 130 is also mounted to gantry robot system 12. Like yoke 100, apparatus 130 (shown in FIG. 10) is coupled to a carriage 132 (shown in FIG. 2) and a mast 134 mounted to the carriage 132 with rotational axes as described for the previous trolley and mast. Laser UT apparatus 130 allows movement in X-axis (along line L), and Y-axis (up and down along line G), and rotational movement (e.g., about arrows 112, 114, 116) by using stepper motors 135. The rotational movement of the laser UT apparatus allows it to reach underside areas of the fuselage while being support by gantry robot system 12 that is above the fuselage, as shown in FIGS. 10, 11 and 12. A mirror 136 of FIG. 10 receives laser energy "L" from within housing 130 and distributes the energy on the scanned surface by mirror rotation, indexing and mast rotation and scanning, as shown in FIG. 12. Reflected laser light provides further diagnostics.

A laser UT gantry robotic system is provided for inspection of both intact airplane and components removed from the airplane. In preferred embodiments of the present invention, component imaging systems such as X-ray, N-ray and laser UT are utilized for pre-inspection of airplane spare components, as well as post-inspection of repaired components removed from the airplane to ensure adequate repair process and procedures.

The embodiments of present invention include robotic imaging inspection methods and systems, such as real-time X-ray, N-ray and laser UT. When used separately, certain imaging inspection methods find certain airplane structural defects. According to certain embodiments of the present invention, N-ray imaging inspection methodology locates and images structural integrity defects such as one selected from a group consisting of internal moisture, corrosion, internal fuel leaks, and voids in sealants. Similarly, real-time X-ray imaging inspection methodology finds and images structural integrity defects such as one selected from a group consisting of moisture, corrosion, cracks, fatigue damage, collateral damage, flaws, deformation, and foreign objects. Laser UT inspection methodology finds and images structural integrity defects such as one selected from a group consisting of disbond, delamination, impact damage, material life, porosity and voids.

Defects are preferably evaluated against a predetermined accept/reject criteria to determine corrective maintenance and repair actions, as explained below in connection with a step 2310 of FIG. 23A. In certain preferred embodiments of the present invention, defects are monitored over time to determine the defect's growth in length, width and depth. A baseline may be accomplished using X-ray, N-ray and laser UT volumetric measurement techniques, and by identifying size (length, width, and depth) and location of each defect in all components of an airplane. This method provides laminography views through the wing or any component part to locate exact position of a defect within multiple layers of a component's structural material. The defect may be identified in multiple material layers existing between the component's inner most layer and outer most layer of material. By way of example, the method provides two dimensional and three dimensional laminography views of a disbond or void within a component's multi-layer composite material to determine length, width and depth of the defect at a specific X-axis, Y-axis and Z-axis position within the material and between specific layers of a component's composite material.

The laser UT methodology locates defect regardless of a composite or metal structure's configuration. When used in combination on any given airplane or component, or when monitoring a partial or complete airplane fleet or partial or complete fleets of like airplanes, various types of structural defects and discrepancies may be identified on a component/sub-component or on a series of multiple components at a single location or on multiple locations on each component/sub-component with high precision to delineate a defect or deficiency trend within the component/sub-component or series of components/sub-components. For example, the defects or deficiencies may be further analyzed and identified by the components'/sub-components' part number, serial number and use on a given airplane's tail number. Each defect's or discrepancy's size may be recorded and tracked by inspection number, number of flying hours, number of takeoffs and landing cycles and number of missions during the component's life cycle. In certain embodiments of the present invention, each defect's or discrepancy's growth in size is recorded and tracked by date and time, inspection, maintenance and repair location, inspection number, number of flying hours, number of takeoffs and landing cycles and number of missions during the component's life cycle.

Future structural defects and deficiencies may be formulated and predicted on a component-by-component basis and may be based on defect growth within a component. Furthermore, a defect growth rate within an airplane component may be predicted, which in turn may restrict an airplane fleet's maximum flight speed to inhibit further defect growth. Predictive analysis may also be used to estimate the time between maintenance for the component, inventory requirement to replace or repair the component or parts within the component, and associated workflow days and budget requirements. Structural problems may be formulated and predicted by model and series of airplane, by matching components' part number and serial number to airplanes' tail number in the airplane fleet. An airplane component's part number, and serial number, and historical inspection, maintenance and repair data is captured, entered or downloaded and stored by date and time, inspection, maintenance and repair location, inspection number, number of flying hours, number of takeoffs and landing cycles and number of missions on an a non-volatile, solid state computer chip containing flash memory and wireless Blue Tooth or other form of wireless communications that is embedded in the component. The computer memory chip is readable by a wireless communication data capture and display device without airplane or component disassembly.

In accordance with embodiments of the present invention, laser UT utilizes a pulsed laser to introduce an ultrasonic sound wave into composite or metal material. A pulse laser source is moved along an airplane or a component part's surface by the means of a translation mirror moving in X and Y position to achieve a roster scanning of the airplane or the component of the airplane. The pulse length for scanning (time the laser beam is on the part's surface) can be accomplished at a rate of up to 240 pulses per second. The present state-of-the-art technologies are limited to surface scanning, and they do not ablate composite materials or surface coatings.

In the current manufacturing process of composite materials to achieve a desired shape, a bond former is utilized to nest composite cloth or prepreg resin systems. This bond former is made of metal or composite material and is coated with mold release to allow the newly cured part to be removed without destroying the part or bond former. The mold release becomes impregnated into the resin system of the new part and must be removed prior to application of paint, adhesives or other coatings to achieve proper bond strength and surface tension for adhesion.

The present state-of-the-art methods of removing mold release or surface coatings such as paint is accomplished by manual and mechanical means such as hand sanding or high pressure media blast. These manual and mechanical stripping methods expose the new part's composite fibers to excessive damage when aggressively attempting to remove mold release from the resin system.

Laser UT to inspect and verify airplane component composite condition is modified and enhanced, in accordance with certain embodiments of the present invention, to include laser ablation to precisely and effectively remove surface coatings on composite material during the inspection process. This can be accomplished, for example, by increasing the pulsed laser output, or modifying the length of the pulse, or a combination of modifying laser output and pulse length. Ablation is based on a gain in power of the light source and pulse rate (pulse length in time on the component's material surface). Ablation power and pulse rate may vary based on the type of material and thickness of the coating that is being removed. Laser UT can measure a coating thickness before and after stripping the coating. As a result, methods, as provided by certain embodiments of the present invention, affect the resin system or matrix only, not the composite fibers of the component's material. As such, the integrity of the component is not affected by this method of coating removal. During manufacturing and repair prior to the airplane component being placed in service, this method provides precise stripping of surface coating, a reduction in manufacturing and repair time, and cost savings during final material surface coating preparation, final material surface tension preparation for adhesive bonding application, and material surface coating stripping in preparation for repair. In-service airplane requires periodic inspection, maintenance and repair which require removal and reapplication of painted or coated services. The method described above provides inspection and removal of paint and other coatings during a single laser UT inspection application.

Considering the drawings, wherein like reference numerals denote like parts throughout the various drawing figures, reference numeral 10 of FIG. 1A is directed to non-destructive inspection and testing systems, according to one embodiment of the present invention, for airplane components and/or sub-components.

Each NDI system discussed above has its own robot. Each individual robot has a "home" position to verify accuracy and to correct possible relocated robot movement (such as from earthquakes). An example of this is the home position fixture for the X-ray and N-ray inspection systems. The home position fixture is preferably inverted "L" shape flat plate steel 180 (which is found in FIG. 2) whose vertical leg 180b is attached to wall 46 with approximately four feet overhang provided by horizontal leg 180a from the wall. The flat steel plate overhang horizontal leg 180a is parallel to the concrete facility floor. A small, about 0.030-inch hole 181 is drilled through the center of an overhang plate 180a. With the X-ray system on, a CRT screen contains crosshairs (like a hunting rifle scope) to locate the crosshairs in the center of the overhang hole at 5× geometric magnification. This provides a home position initialization step (calibration) and is preferably performed prior to each and every airplane inspection and also for all robots and each inspection method (X-ray, N-ray and Laser UT). Laser alignment relies on a uniform thickness plate 183 having at least two variations $V_1$ and $V_2$ from the uniform thickness at known locations. The laser, when scanning the variations (e.g., a counter-bore), preferably reflects the known variations as a function of relative length and distance. In FIG. 2A, rails 42 can be aligned by oval slots 51 allowing motion of rail 42 relative to its support plate 44. A J bolt supports rail 42 and plate 44 in wall 58. A threaded free end of J bolt 50 includes washers "W" and nuts "N" for vertical and lateral truing.

As previously stated, the present invention has at least one and preferably three or more robots. The use of multiple robots provides several advantages. By way of example, multiple robots allow simultaneous inspection of several areas of an airplane, thereby reducing the time required to inspect an airplane. As another example, multiple robots avoid the need for a single long supporting beam, which would reduce positioning accuracy and repeatability. As yet another example, multiple robots allow each robot to be specifically designed to inspect particular areas of an airplane, thereby allowing accommodation of special attributes of various areas.

Corbels 12, 43 and rails 42 are provided to support multiple robots. The walls 58, ceiling 59, and hanger door entrance 61 are designed to support corbels and rails, which permit linear translation. The location of corbels within the structure, e.g., an airplane hanger, is designed to accommodate structural loading (due to weight of the robot, robotic movement yielding unaccepted resonate frequencies, etc.) while maintaining accuracy and repeatability of robot position over six axes of movement within a narrow range of tolerances to plus or minus about 0.120 inches. The structure accommodates structural loading of various types, for example floor loading, wind loading and loading from the mass of the robots.

The inspection facility is designed to protect personnel from radiation hazards (including X-rays and neutrons). Shielding 63 (of FIG. 2A), including shielding of walls, doors, and windows is provided. Interlocks 201 (of FIG. 3) are provided to prevent the emission of radiation when personnel might be endangered, such as when a door is opened. Other measures, such as key controls and password authentication are provided to prevent emission of radiation or other potentially hazardous activities, such as motion of robotic systems, without approval of authorized personnel. Radiation monitoring and alarm systems 203 are provided to detect abnormal radiation levels and provide warning.

One example of a technique used to provide radiation safety even though the walls, doors, ceiling and viewing windows are designed to accept maximum radiation at a distance of three feet, and do not allow X-ray or N-ray sources to be aimed at these surfaces. In preferred embodiments of the present invention, the robot positioners only allow the radiation source to be aimed toward concrete bay floor 57, or airplane structure. This is accomplished by programming the robotic movement throughout the facility. Other than in the scan plan, which is discussed in greater detail below, during the airplane inspection operation, the radiation sources are non-operational. This is called the "Robotic Approach." Both X-ray and N-ray sources are on systems or on/off systems. The on/off systems may be energized at the beginning of the scan plan inspection operation or calibration. Override of this radiation protection system is accomplished for robot or source maintenance purposes, and controlled by software code known preferably to the first level supervisor and maintenance personnel.

A method for design of a non-destructive inspection, testing and evaluation system for airplane component having a precision robotic system is provided. The dimensional and structural requirements of a building are determined, and a preliminary design for the building is made. The preliminary design for the building is analyzed to identify any frequencies (earthquake zones) at which such a building might resonate. For example, a technique such as finite element frequency analysis may be employed. Based on the results of the analysis, the preliminary design of the building may be modified to correct any deficiencies.

The dimensional, structural, and functional requirements for robots to be housed within the building are determined, and a preliminary design of the robots is made. The preliminary design of the robots is analyzed to identify any frequencies at which such robots might resonate. Any interaction between the resonant frequencies of the building and the resonant frequencies of the robots are analyzed. Based on the results of the analysis, the preliminary design of either or both of the building and the robots may be modified to correct any deficiencies.

The dimensional, structural, and functional requirements of any end effectors mounted on the robots are determined, and a preliminary design of the end effectors is made. The preliminary design of the end effectors is analyzed to identify any frequencies at which such end effectors might resonate. Any interruption between other elements, such as the building or the robots, is analyzed. Based on the results of the analysis, the preliminary design of any or all of the building, robots, or end effectors may be modified to correct any deficiencies.

Another factor to be considered is the type of earthquake region in which the facility is to be located. Different earthquake regions may exhibit earthquakes having different characteristics, for example earthquakes have vibration and motion of predominantly a certain frequency range. This frequency range is determined for the location at which the facility is to be located based on geological data. The preliminary designs of the building, robots, and end effectors are analyzed base on anticipated excitation from earthquakes. Based on the results of the analysis, the preliminary design of any or all of the building, robots, or end effectors may be modified to correct any deficiencies.

When the preliminary designs of the buildings, robots, and end effectors are completed, modeling of the entire system may be performed to assure accuracy and repeatability of robot positioning. Oscillatory excitation of the system components resulting from robot motion and acceleration and deceleration may be analyzed. Designs of the system components may be modified to maximize desirable characteristics, such as accuracy and repeatability of robot positioning, while minimizing undesirable characteristics, such as unwanted oscillatory excitation of system components.

Figure 16:
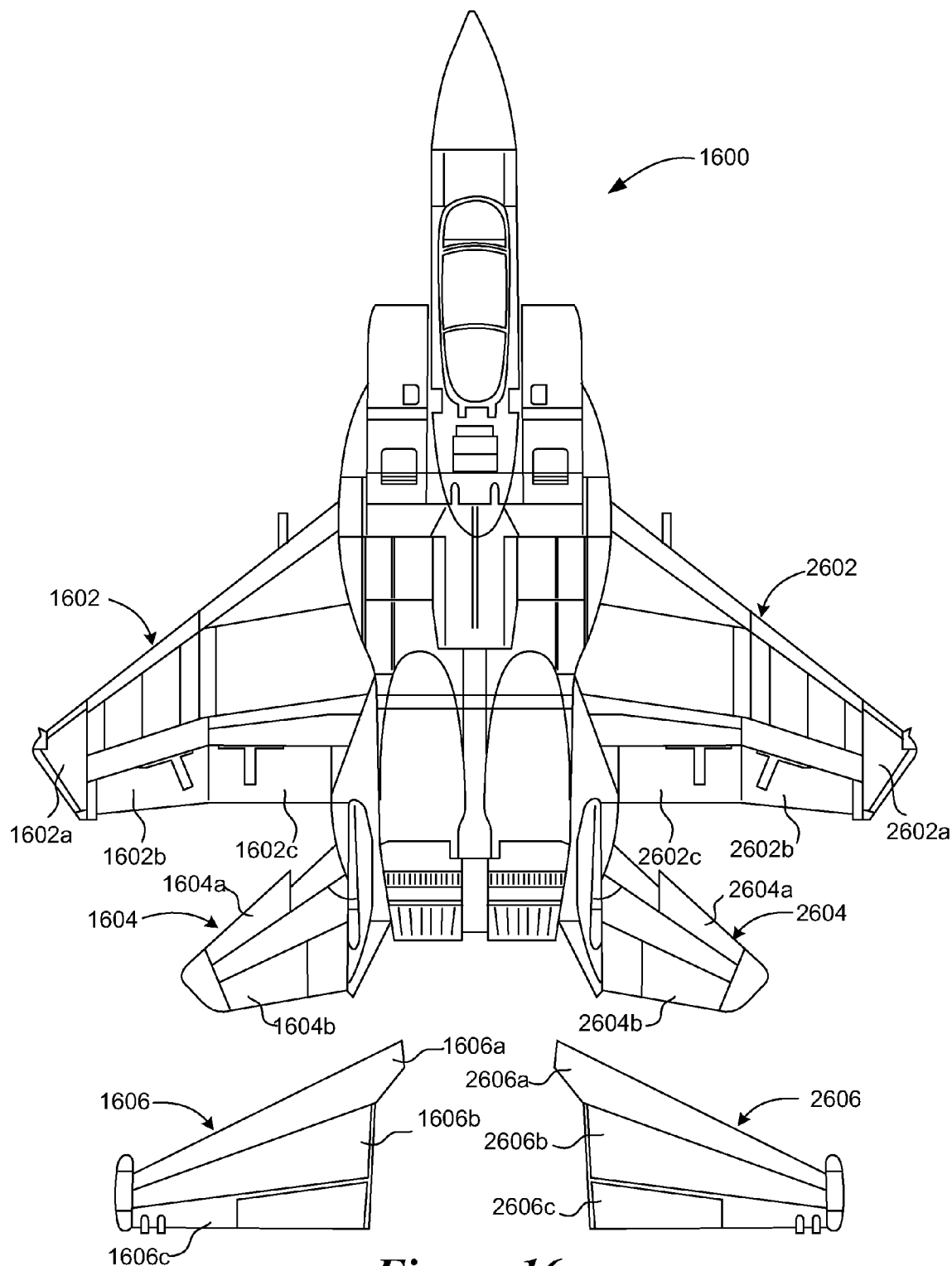
FIG. 16 shows a plan view of an exemplar airplane having various components and sub-components.

FIG. 16 shows a plan view of an exemplar airplane 1600 that is subject to inspection in the above-described robotic envelope as part of fleet maintenance. To facilitate discussion, only certain major components and sub-components are described below.

Airplane 1600 includes various component and sub-components. As shown in FIG. 16, airplane 1600 includes components, such as a left wing 1602, a right wing 2602, a left horizontal stabilator or stabilizer 1604 (as those terms are interchangeably used in the specification), a right horizontal stabilizer 2604, a left vertical stabilizer 1606 and a right vertical stabilizer 2606. These components further include sub-components. By way of example, left wing 1602 includes sub-components such as a left wing tip 1602a, a left aileron 1602b, a left flap 1602c. Similarly, right wing 1602 includes sub-components such as a right wing tip 2602a, a right aileron 2602b, a right flap 2602c.

As another example, left horizontal stabilizer 1602 includes sub-components, such as a left leading edge box 1604a and a left aft box 1604b, and right horizontal stabilizer 2604 includes sub-components, such as a right leading edge box 2604a and a right aft box 2604b. Left and right vertical stabilizers 1606 and 2602 include sub-components such as, a left forward box 1606a, a left torque box 1606b, a left aft box 1606c, a right forward box 2606a, a right torque box 2606b, and a right aft box 2606c, respectively.

Exemplar airplane 1600 resembles an F-15 aircraft, but airplane 1600 could be any airplane or aircraft and may well include a commercial airplane. Those skilled in the art will appreciate that different airplanes include different components or sub-components and even if different airplanes have the same components or sub-components, they may have different component or sub-component sizes. By way of example, although an F-15 has left vertical stabilizer (e.g., denoted by reference numeral 1606 in FIG. 16) and right vertical stabilizer ((e.g., reference numeral 2606 in FIG. 16), a commercial airplane has only a single vertical stabilizer. The systems and methods of the present invention, nevertheless, allow for effective automatic fleet inspection despite these different component/sub-component configurations in different types of airplanes.

NDI systems and processes of the present invention preferably contain features to perform non-destructive inspection and testing of intact airplanes or of components and/or sub-components removed from an airplane. Such inventive systems and methods include a database which contains electronic information relating to at least one profile of a prototypical airplane or component (a comparison standard), which is maintained in an enclosure at constant environmental conditions (e.g., constant temperature, humidity and pressure).

Although preferred embodiments of the inventive methods and systems apply to fleet of airplanes, the present invention is not so limited. Methods and systems of the present invention apply to aircrafts and other types of in-flight vehicles (e.g., helicopters, Unmanned Aerial Vehicles and spacecrafts). The terms "airplane" and "aircraft" have been used interchangeably in the specification. Furthermore, as the terms "airplane" and "aircraft" are used in the specification, in addition to the in-flight vehicles mentioned above, they include manned or unmanned vehicles capable of flight by gaining support from air, and spacecrafts that are capable of sub-orbital or orbital space flight.

Figure 14:
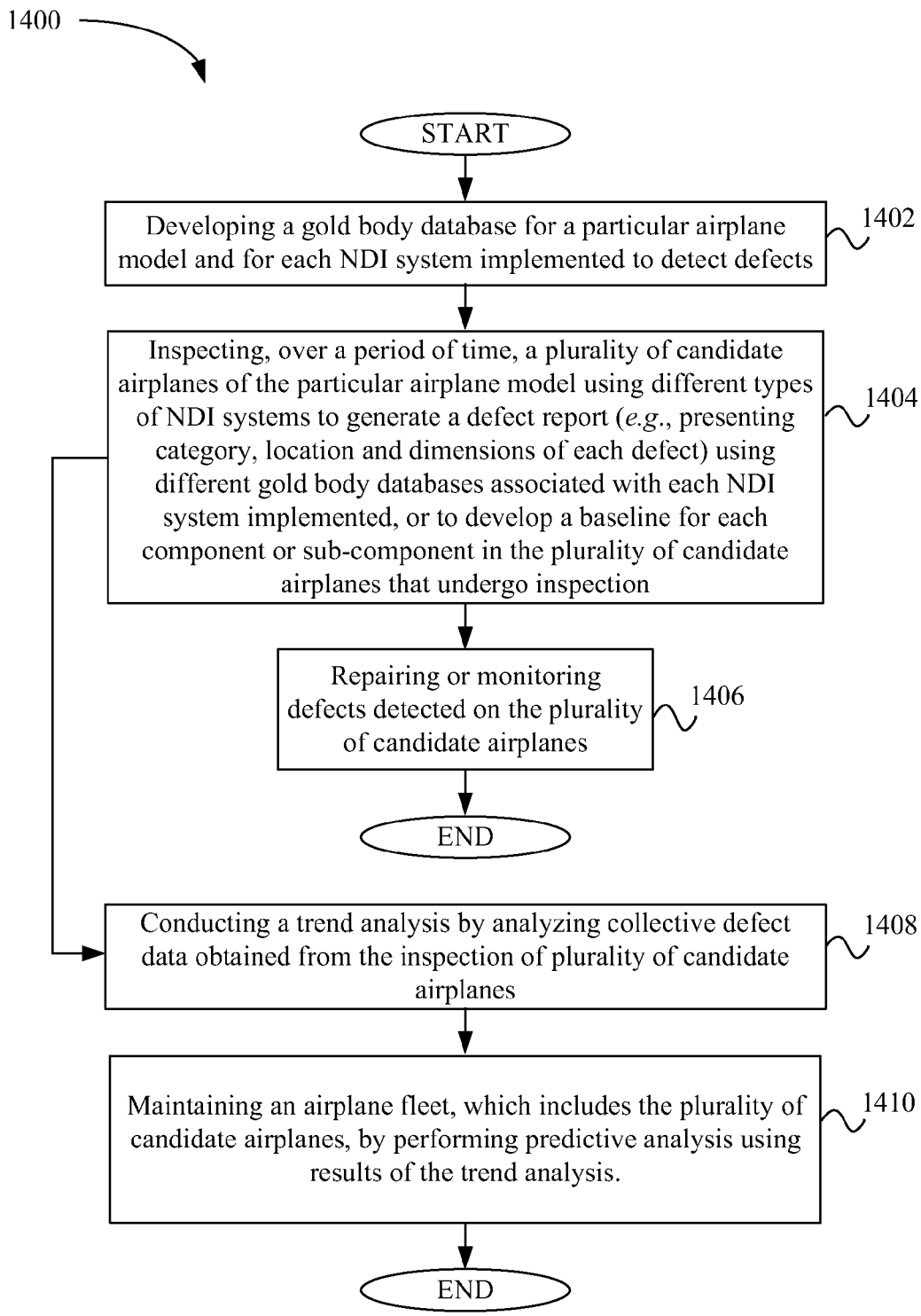
FIG. 14 is a process flow diagram for an airplane fleet management process, in accordance with preferred embodiments of the present invention.

FIG. 14 is a process flow diagram 1400 for maintaining an airplane fleet, according to preferred embodiments of the present invention. An airplane fleet includes a plurality of candidate airplanes. In this embodiment, process 1400 begins with a step 1402 which includes developing a gold body database for a particular airplane model and for each NDI system implemented to detect defects. In other words, a gold body database is developed for a particular airplane model using a particular NDI system (e.g., an X-ray or an N-ray inspection system). By way of example, if an X-ray and an N-ray inspection system are used to inspect candidate airplanes of a particular model, then according to step 1402 a first gold body database is developed for the X-ray inspection system and a second gold body database is developed for the N-ray inspection system. As will be explained later, the gold body database developed in this step serves as a "reference database," during subsequent inspection or defect analysis steps. A more detailed explanation of the development of a gold body database is presented below in connection with a description of FIG. 15.

Next, a step 1404 includes inspecting, over a period of time, a plurality of candidate airplanes of the particular model using different types of NDI systems to perform one step selected from a group consisting of generating a defect report using different gold body databases associated with each NDI system, and developing a baseline for each component or each sub-component in the plurality of candidate airplanes that undergo inspection. In other words, results (which preferably include a defect report and/or a baseline) from the inspection of candidate airplanes using a particular NDI system is compared to the gold body database developed for that NDI system and for the particular model of the candidate airplanes.

A step 1406 includes repairing or monitoring defects detected on the plurality of candidate airplanes as will be explained in greater detail in connection with FIGS. 23 and 24.

Preferably on a parallel track to step 1406, a step 1408 is performed and includes conducting a trend analysis by analyzing collective defect data obtained from the inspection of plurality of candidate airplanes. Trend analysis includes at least one analysis selected from a group consisting of applying Boolean logic rules, tracking categories of defects found in a component or a sub-component of the plurality of candidate airplanes through an overlay of images obtained from one or more systems selected from a group consisting of an X-ray system, an N-ray system and a laser UT inspection system, tracking single site defect location or multi-site defect locations, tracking defect dimension, tracking growth of defect over a period of time, tracking low observable coatings on plurality of candidate airplanes, tracking paint deficiencies on plurality of candidate airplanes, applying Boolean logic rules, and conducting statistical analysis. In preferred embodiments, trend analysis of the present invention assigns a defect detected to one of the candidate airplanes by associating that defect with at least one item selected from a group consisting of airplane manufacturer, airplane type, airplane model, airplane tail number, airplane part noun, airplane part serial number, and airplane component or sub-component location by number. More details regarding trend analysis have been provided above and are also provided below in a discussion relating to FIG. 22.

In a preferred embodiment, inventive process 1400 concludes with a step 1410 which involves maintaining an airplane fleet by performing predictive analysis, which uses results of trend analysis that was conducted in step 1408. Predictive analysis includes at least one analysis selected from a group consisting of applying Boolean logic rules, projecting remaining life of components or sub-components of said plurality of candidate airplanes, projecting remaining life of said plurality of candidate airplanes, projecting when said components or said sub-components of said plurality of candidate airplanes should be removed from service, projecting load limitations for said components or said sub-components of said plurality of candidate airplanes, projecting needed maintenance cycles for said plurality of candidate airplanes and projecting spare parts inventory demand for said plurality of candidate airplanes, projecting needed maintenance resources during maintenance cycles for the plurality of candidate airplanes.

In certain embodiments of the present invention, Boolean logic rules are applied to conduct trend analysis on a plurality of candidate airplanes, which belong to an in-service airplane fleet. By way of example, for candidate airplanes in an F-15C airplane fleet, X-ray and N-ray robotic inspection systems and methods are used to inspect a left and a right horizontal stabilizer's leading edge box to detect defects. A sum of detected defects for each type of defect (i.e., adhesive crack, blown core, cell corrosion, crack, damaged core, moisture, skin corrosion, void, etc.) and their respective locations on the X and Y coordinates from the origin are recorded. Next, results by type and location of defects are overlaid on a digital simulated image of the airplane's left and right horizontal stabilizers, allowing a visual identification and statistical analysis of trends for engineering analysis. In preferred embodiments of the present invention, additional steps follow the step of forming digital simulated image of the airplane's component or sub-component. For example, a step of monitoring airplane fleet condition and identifying fleet trends, as they relate to defects, flaws and deficiencies present in a region of a component or a sub-component, are carried out. As another example, a step is carried out to automatically electronically transmit data, digital image and statistical analysis to engineering computer systems for engineering analysis. In other embodiments of the present invention, certain data, digital image and statistical analysis is sent to a governmental regulatory body (e.g., Federal Aviation Administration) to meet regulatory reporting requirements.

According to preferred embodiments of the present invention, Boolean logic rules may also be used for conducting a predictive analysis. In the above example, overlaying certain defect properties on the digital simulated image and statistical analysis of the left and right leading edge box allows for certain types of predictive analysis, such as determination of need to ground fleet, restrict fleets' operational threshold, and determination of maintenance cycle for the fleet (e.g., every 6 months or 12 months), based on engineering analysis.

Those skilled in the art will appreciate that the above example of F-15C is similarly applied to an F-35A fleet, where a laser UT robotic inspection system is used for inspecting a right wing leading edge of candidate airplanes in the F-35A airplane fleet. Predictive analysis and trend analysis for the F-35A airplane fleet is carried out in a manner that is very similar to those described above for the F-15C airplane fleet.

Figure 15:
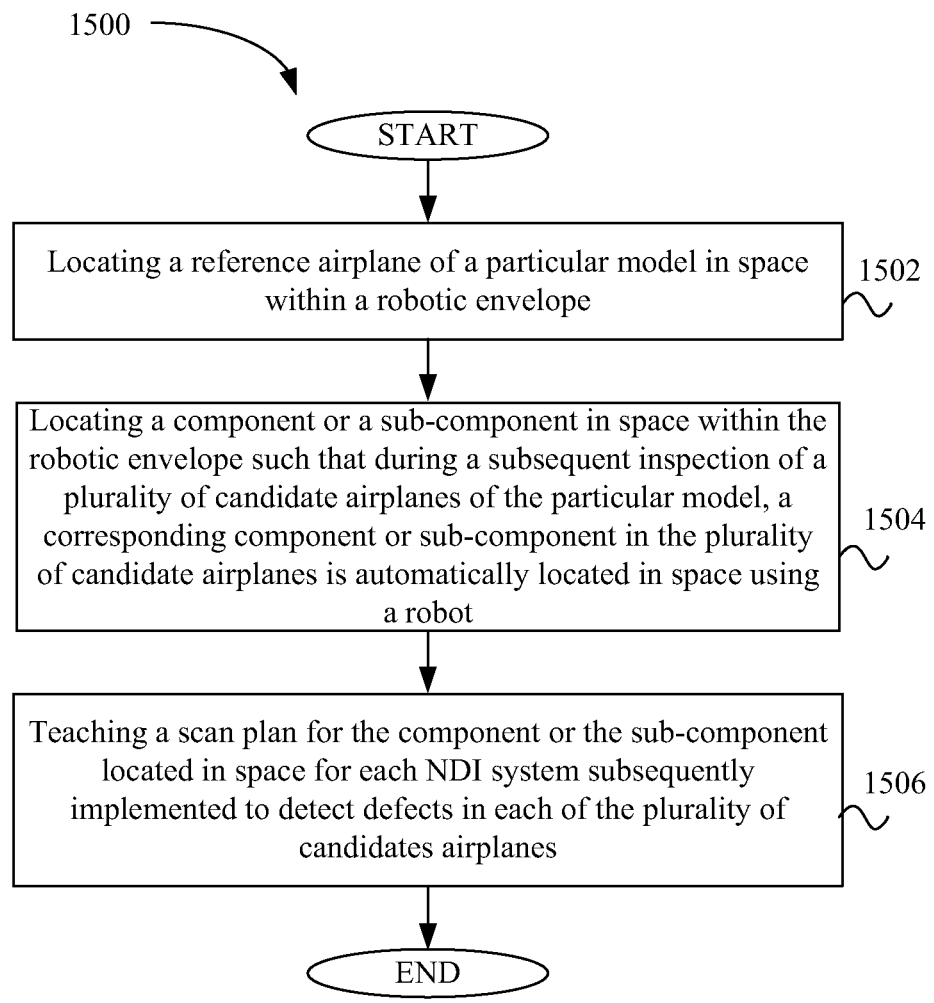
FIG. 15 is a process flow diagram for a method of developing a gold body database, in accordance with preferred embodiments of the present invention, of a particular airplane model and that is developed for each NDI system implemented to detect defects.

FIG. 15 shows a process flow diagram for a process 1500, according to a preferred embodiment of the present invention, for developing a gold body database. Process 1500 includes a step 1502 which includes locating a reference airplane of a particular model in space within a robotic envelope. By way of example, each model and series airplane is located to a specific spot for a nose gear and the main landing gear tires are aligned. The airplane components/sub-components may be aligned to lines on the floor. Other candidate airplanes of the same model and series, which are subsequently inspected, will also use those lines on the floor for rough positioning. The airplane is then jacked into position using jacks 205 (as shown in FIG. 3), taking the load off of the tires and actuators. Thus, the airplane becomes fixed in position and can no longer move due to change in tire pressure attributed to environmental changes or loss of hydraulic pressure in the actuators. Edges which define the boundary of the plane are taught to one or more robots used in one or more NDI inspection systems.

Next, a step 1504 includes locating a component or a sub-component in space within the robotic envelope such that during a subsequent inspection of candidate airplanes of the particular model, a corresponding component or sub-component in candidate airplanes is automatically located in space using a robot. In this step, at least two or more edges of a component or a sub-component are preferably taught to each of the robots associated with an NDI system.

A step 1506 includes teaching a scan plan for the component of the sub-component located in space. The scan plan in this step is taught for each NDI system that is subsequently implemented to detect defects in candidate airplanes. In this manner, process 1500 is carried out for each NDI system that is implemented for defect detection, which in turn is carried out for effective airplane fleet management.

Figure 17:
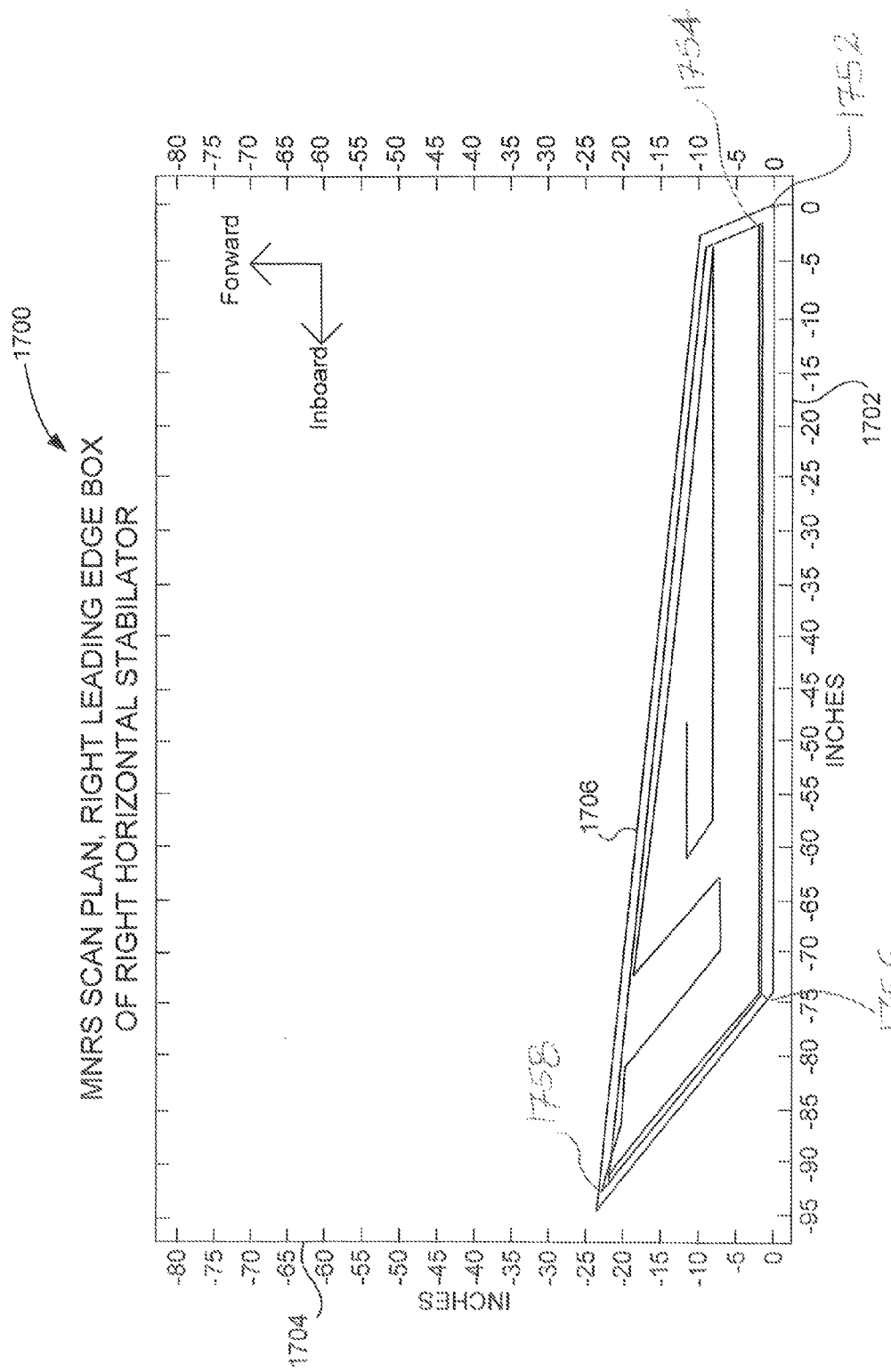
FIG. 17 shows a scan plan, in accordance with preferred embodiments of the present invention, for inspecting an exemplar right leading edge box of an airplane stabilator using a Maneuverable N-ray Radiography System ("MNRS").

FIG. 17 shows an exemplar scan plan 1700 developed for a right leading edge box (e.g., leading edge box 2604a of FIG. 16) of a right horizontal stabilizer (e.g., horizontal stabilizer 2604 of FIG. 16) using MNRS. Scan plan 1700 is represented in FIG. 17 in graphical form, i.e., displacement of an MNRS robot along a Y-axis 1704 versus displacement of the MNRS robot along an X-axis 1702. In step 1506 of FIG. 15, scan plan like the one shown in FIG. 17 is taught to an MNRS robot and the taught information, a zero-zero coordinate in the x-y plane 1752 and registration points 1754, 1756 and 1758, are is saved as part of the gold body database. Lines 1706 represent a path of movement from one registration point 1754 to another registration point 1756 and to yet another registration point 1758 that is traced by the MNRS robot, as it scans the right leading edge box during inspection. Those skilled in the art will appreciate that scan plan 1700 is an exemplar graphical representation of the MNRS robot's plan of movement during a subsequent inspection process and that a scan plan is created for each or critical components and/or sub-components of a candidate airplane.

Figure 18:
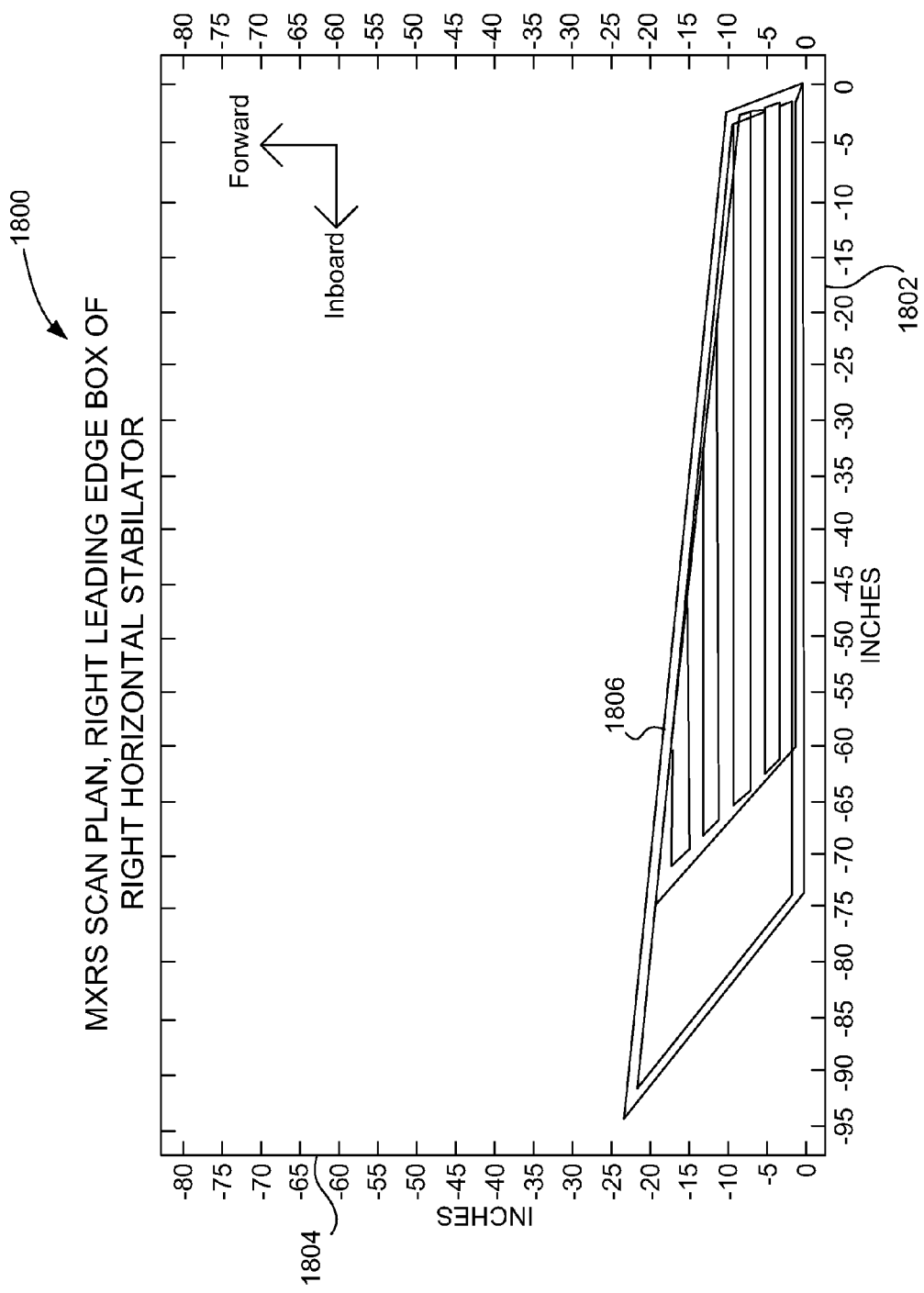
FIG. 18 shows a scan plan, in accordance with preferred embodiments of the present invention, for inspecting an exemplar right leading edge box of an airplane stabilator using a Maneuverable X-ray Radiography System ("MXRS").

FIG. 18 shows another exemplar scan plan 1800 developed for a right leading edge box (e.g., leading edge box 2604a of FIG. 16) of a right horizontal stabilizer (e.g., horizontal stabilizer 2604 of FIG. 16) using MXRS, as opposed to using MNRS as described in connection with FIG. 17. Like scan plan 1700, scan plan 1800 also is represented in FIG. 18 in a graphical form, i.e., displacement of a MXRS robot along a Y-axis 1804 versus displacement of the MXRS robot along an X-axis 1802. Scan plan 1800 is also taught to the MXRS robot and is saved as part of the gold body database. Lines 1806 represent a path of movement traced by the MXRS robot, as it scans the right leading edge box during inspection.

Scan plans are different for each robotic imaging method such as for N-ray, X-ray or laser UT because of the field of view and the area of interest due to the type of airplane structure. Nonetheless, the X and Y-axis coordinates on the component/sub-component or panel remains the same. As will be explained later, this allows the results of each inspection method (e.g., X-ray, N-ray, Reverse Geometry and laser UT) to be identified on a master layout, allows overlaying results of the inspections to identify multi-site damage and allows downloading the results of each airplane inspected to overlay on the same component, sub-component or panel for determining trend analysis and model airplane fleet condition.

Use of scan plans facilitates automatic inspection of airplane fleets. By way of example, once the whole airplane has been taught to the system of the present invention, the scan plans of each NDI method can be applied in part or whole on candidate airplanes to carry out inspection.

Inspection of a component or a sub-component using a particular NDI system produces, among other things, a defect report for that component or sub-component and for that particular NDI system. A defect report contains at least one item selected from a group consisting of category of defect, defect location and defect dimensions. Defect location is preferably a location of defect in (x, y) coordinates of the inspected component or sub-component. A defect map may be formed for a component or sub-component by aggregating one or more defect locations. The defect map so formed is associated with the particular NDI system used for defect detection.

Figure 19:
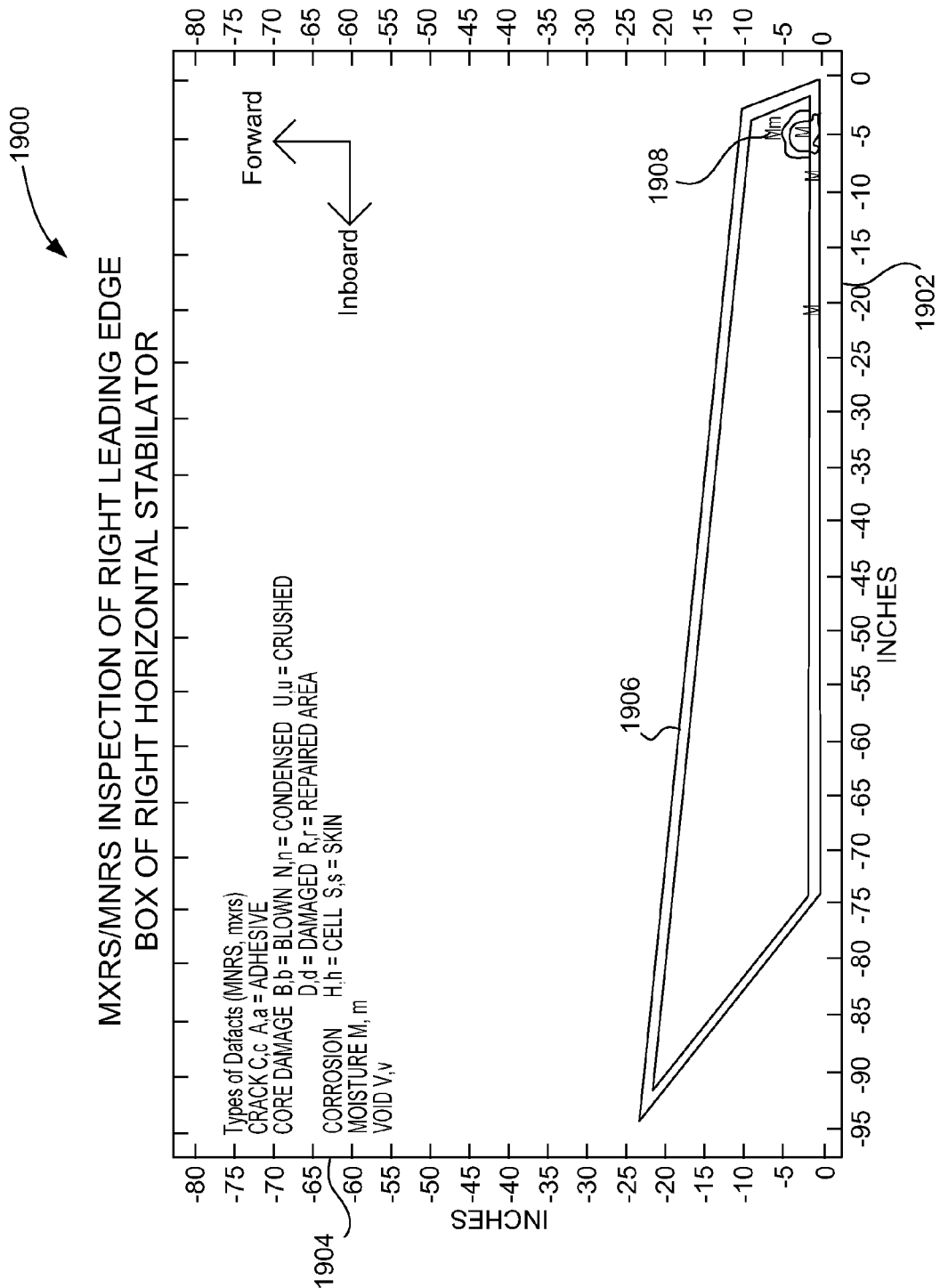
FIG. 19 shows a defect map, according to preferred embodiments of the present invention, prepared by overlaying defects found by NNRS and MXRS inspection of an exemplar right leading edge box of an airplane stabilator.

Two or more defect maps, each generated from a different NDI system, may overlay on a single map to produce an integrated map, which serves as a historical record for that component or sub-component. FIG. 19 shows an integrated defect map 1900 produced from overlaying two defect maps produced by inspection of a right leading edge box of a right horizontal stabilizer using MXRS and MNRS. Integrated map 1900 is a graphical representation as it shows location of defects by referring to their locations on the X-axis and Y-axis. As shown in FIG. 19, integrated map 1900 has defined thereon shape 1906 of the inspected sub-component, i.e., a right leading edge box of a right horizontal stabilizer. Inside shape 1906, one or more defects are presented. Integrated map 1900 preferably also presents a legend to convey the meaning of one or more symbols or letters placed at a defect location. By way of example, at one defect location 1908, which is labeled "M" and "m" and has coordinates of about (−5,−5), both MNRS and MXRS inspections convey that moisture is present at that location.

Figure 20:
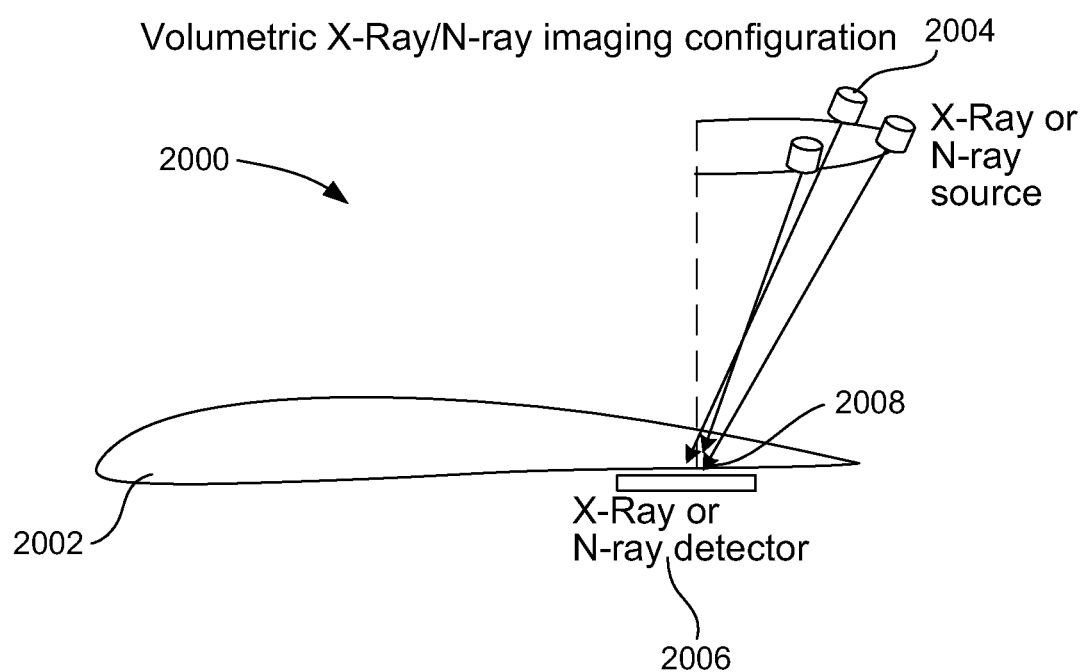
FIG. 20 shows an X-ray and N-ray imaging configurations, according to preferred embodiments of the present invention, implemented to obtain a volumetric measurement.

FIG. 20 shows a volumetric X-ray or N-ray imaging configuration 2000, which may be used to provide a baseline image obtained during component and/or sub-component inspection. In this configuration, a radiation imaging source 2004, which can be an X-ray imaging source or an N-ray imaging source, is used to inspect a sub-component 2002. Radiation source 2004 is positioned on one side of sub-component 2002 such that a beam of radiation is incident upon the sub-component during an imaging process. A radiation source detector 2006 disposed on the other side of sub-component 2002 detects the radiation that is transmitted through the sub-component. During a volumetric measurement process to create a three-dimensional image of a defect, radiation source 2004 articulates around a tool point 2008.

Volumetric measurement, according to one embodiment of the present invention, is accomplished by precise robotic articulation. Precise robotic articulation is accomplished by having a robot rotate 360 degrees in a circle about a tool point, causing both radiation source 2004 and detector 2006 to similarly rotate.

Certain embodiments of the present invention include two dimensional ("2D") and three dimensional ("3D") data capture and imaging inspection methods and technologies. Data identifying the size of the defect or discrepancy is captured in the X-axis, Y-axis and Z-axis. Analog film and digital images capture and show the defect or discrepancy in X and Y coordinates. Once the defect or discrepancy is identified the system is capable of articulating in a circle about the defect tool point or object capturing an image of the tool point or object at a minimum of 8 imaging stations or at least every 45 degrees on the circle. 3D images may be reconstructed by articulating in a circle about the defect tool point or object capturing an image of the tool point or object at a minimum of 16 imaging stations or at least every 22.5 degrees on the circle. Adjacent imaging stations images are then super imposed to provide a 3D image. Computer generated reconstruction of multiple images is used to generate a laminography image. The defect or discrepancy's location within a component is identified by X-axis, Y-axis and Z-axis distance from the component's X and Y origin and the layers within which it resides between the component's innermost layer and outermost layer. The data, film and images showing the defect's and discrepancy's size and location within the component is recorded with the component's part number and serial number, and the component is recorded at the time of the inspection with the airplane's tail number. The component may be used on multiple airplanes, during their life cycle, by being disassembled from the airplane, repaired or refurbished, and then placed into a rotational spares inventory for use on any airplane undergoing maintenance and repair.

Display of images is accomplished utilizing 2D and 3D front or rear projection screens, displays and monitors. The viewer may wear active shudder glasses or passive Polaroid glasses when viewing projection screens, display and monitors requiring these eyewear devices. X-ray and N-ray scan plans are modified to accomplish this task. These methods may be utilized when capturing and viewing real time or offset images, such as volumetric measurement that detects and provides data and image capture of the length, width and depth of a defect or discrepancy in structural material. The data and image capturing and viewing methods are commonly used in the inspection of airplane components comprised of multi-layered metal and composite structural material. This method identifies defect and discrepancy size and location to monitor component maintenance, assist implementation of pre-repair procedures and repair technologies, and validate post repair procedures.

Figures 21A, 21B:
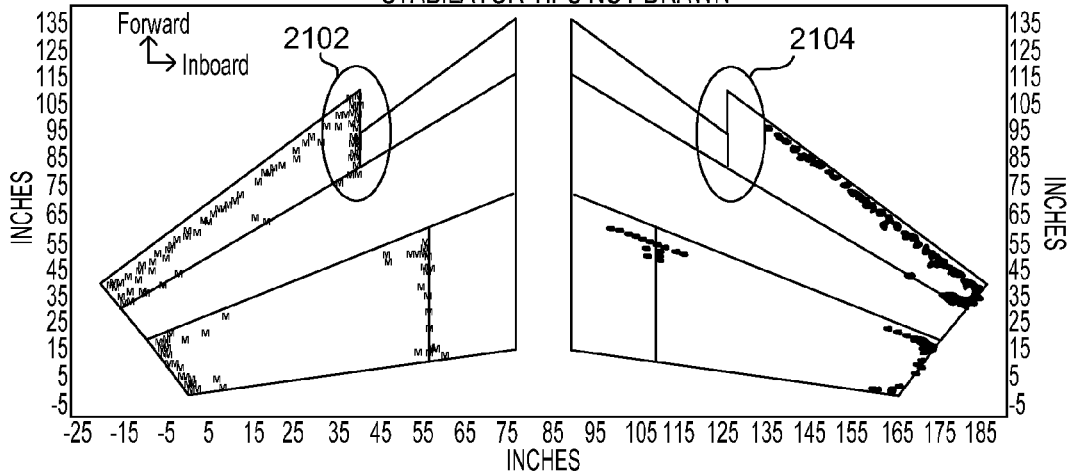
FIG. 21A shows a defect map, according to preferred embodiments of the present invention, prepared by overlaying defect (e.g., moisture, corrosion and voids) detection carried out by MNRS and MXRS inspection of an exemplar horizontal stabilator.
FIG. 21B shows an exemplar data summary of various defects found in an exemplar horizontal stabilator.

FIG. 21A shows a comparison between two components defect maps, one map for a left and another map for a right horizontal stabilizer (e.g., map for left horizontal stabilizer 1604 juxtaposed to a map for right horizontal stabilizer 2604 shown in FIG. 16). The component defect map shows a left region 2102 in a left leading edge of the left horizontal stabilizer and a corresponding right region 2104 in a right leading edge of the right horizontal stabilizer. Left region 2102 includes moisture defects, which are not found in the corresponding right region 2104. While not wishing to be bound by theory, presence of such defects in one region and absence of them in a second region convey that they are manufacturing defects. As a result, defect analysis of the present invention provides a feed-back loop to the manufacturing process regarding the amount and types of defects being introduced during manufacturing, and the repair process will be different.

FIG. 21A shows, among other things, results of mobile airplane inspection, and the comparison of findings of left and right horizontal stabilizer components. It is noteworthy that defect locations are not similar in comparison. According to preferred embodiments of the present invention, engineering disposition investigates and determines why certain defects, such as fatigue, defects from use of improper materials, and defects resulting from manufacturing and assembly process, exist or exist in one region, but not in another corresponding region.

FIG. 21B is a tabular representation of summary of defects found in a right horizontal stabilizer. The summary of defects is broken down into sub-components, having those that are disposed on the left side juxtaposed with those that are on the corresponding right side of the airplane. Furthermore, for each sub-component, number of defects that belong to a particular defect category (e.g., adhesive crack, blown core, cell corrosion, crack, damaged core, moisture, skin corrosion and void) are also tracked and summarized. Further still, summary of defects also informs regarding the number of defects found by MXRS inspection (shown in FIG. 21B as "MX") and by MNRS inspection (shown in FIG. 21B as "MN"). As an example, FIG. 21B shows that the number of corroded cells found in the left aft box using MXRS is 13, and using MNRS is 3. It is believed that a significant difference in the results between MXRS and MNRS inspection allows for various possible conclusions, all of which inform the manufacturing and repair process.

FIG. 22 presents an exemplar trend analysis of 50 airplanes of an airplane fleet. All the various components and sub-components therewithin are presented along a left column, and in the remaining columns an analysis is presented for ten, twenty, thirty, forty and fifty airplanes. As an example, a trend analysis for forty airplanes identifies the defect components. With regard to wing components, trend analysis shows that 30% of the flaps, 85% of ailerons and 43.8% of the wing tips are defective. Similarly for horizontal stabilizers, trend analysis shows 66.3% of aft boxes and 75% of leading edge boxes are defective. For vertical stabilizers, trend analysis shows that 50% of forward boxes, 30% of torque boxes, and 55% of aft boxes are defective. As mentioned above, for each component and/or sub-component, FIG. 21B provides the types of defects found in the components/sub-components. With regard to the aft and leading edge boxes of a horizontal stabilizer, FIG. 21B shows that defects are primarily moisture sites and skin corrosion.

As mentioned before, trend analysis allows monitoring airplane fleet condition and identifying fleet trends, as they relate to defects, flaws and deficiencies present in a region of a component or a sub-component. Such analysis is based on developing results by type and location of defects. Where an airplane's horizontal stabilizers are the component of concern, it has been explained that these results may be overlaid on a digital simulated image of the left and right horizontal stabilizers, allowing a visual identification and statistical analysis of trends for engineering analysis. Boolean logic rules, which may be applied on type of defect, defect severity, and defect frequency (a statistically monitored condition), facilitate prediction or, in the alternative, projection of maintenance activities to effectively manage an airplane fleet. Maintenance activities of the present invention include, but are not limited to, grounding an airplane fleet, restrict a fleet's operational thresholds that govern flight loads, and electronically trigger maintenance planning, execution, and reporting. In other embodiments of the present invention, Boolean logic rules determine a recommended inspection frequency to monitor the fleet's defect condition (e.g., defect growth), and/or maintenance or repair treatment plan.

The following Boolean logic algorithm is based on the results of trend analysis and represents an example of maintenance and treatment plan implemented according to the present invention for an in-service F-15C aircraft fleet (referred to as "F-15C Fleet" below):

If F-15C Fleet LHS SC> or =5, and if ML>8%, then F-15C Fleet LHS TCTO XI and NI=12 and ALC-I99061-02; and if ML<8%, then F-15C Aircraft LHS ALC-R890444-01; and if ML>8%, then F-15C Aircraft LHS ALC-RR890526-01; and if ML>10%, then F-15C Aircraft T=80%; and then F-15C Fleet XI and NI=60 and ALC-M890538-00;

If F-15C Fleet LHS SC<5, if ML<8%, then F-15C Aircraft ALC-R890444-01 and if ML>8%, then F-15C Aircraft LHS ALC-RR890526-01, and if ML>10%, then F-15C Aircraft T=80%, and then F-15C Fleet XI and NI=60 and ALC-M890538-00.

According to this algorithm, if skin corrosion (which is denoted by "SC" above) is detected in a left horizontal stabilizer ("LHS") in 10% or more of 50 F-15C aircrafts ("F-15C aircrafts") belonging to the in-service F-15C aircraft fleet, then different recommended actions are possible for the airplane fleet and a particular airplane, depending on results of different defect measurements. If material loss ("ML") is greater than 8% for the entire fleet, then an inspection by X-ray inspection ("XI") and N-ray inspection ("NI") for the entire F-15C aircraft fleet is scheduled to occur within 12 months under a Time Compliant Technical Order ("TCTO"), and pursuant to treatment plan ALC-I99061-02. If a material loss is less than 8%, however, then for the F-15C aircraft, which satisfies the material loss condition, an instruction is provided to repair the moisture intrusion entry path in the left horizontal stabilizer pursuant to ALC-R890444-01.

For a particular aircraft, which suffers from a material loss that is greater than 8%, then left horizontal stabilizer is scheduled for repair and replacement pursuant to treatment plan ALC-RR890526-01. Furthermore, if the material loss for that aircraft measures greater than 10%, an instruction is provided to reduce in-flight operational threshold thrust ("T") of that aircraft to 80% of maximum performance until F-15C aircraft completion of left horizontal stabilizer's replacement. For this material loss condition, after left horizontal stabilizer repair pursuant to treatment plan ALC-R890444-01 or replacement and repair pursuant to treatment plan ALC-RR890526-01, as the case may be within the twelve-month maintenance cycle, an inspection by X-ray inspection ("XI") and N-ray inspection ("NI") for the entire F-15C aircraft fleet is scheduled to occur thereafter in sixty months pursuant to treatment plan ALC-M890538-00.

In the same example, if skin corrosion is detected in the left horizontal stabilizer in less than 10% of 50 aircrafts of the F-15C aircraft fleet, and if material loss for the F-15C aircraft fleet is less than 8%, then an instruction is provided to repair the moisture intrusion entry path in the left horizontal stabilizer of each detected F-15C aircraft pursuant to ALC- R890444-01. For a particular F-15C aircraft, which suffers from a material loss that is greater than 8%, then left horizontal stabilizer is scheduled for repair and replacement pursuant to treatment plan ALC-RR890526-01. Furthermore, if the material loss for that aircraft measures greater than 10%, an instruction is provided to reduce in-flight operational threshold thrust ("T") of that aircraft to 80% of maximum performance until completion of left horizontal stabilizer's replacement. For this material loss condition, after left horizontal stabilizer repair pursuant to treatment plan ALC-R890444-01 or replacement and repair pursuant to treatment plan ALC-RR890526-01, as the case may be within the twelve-month maintenance cycle, an inspection by X-ray inspection ("XI") and N-ray inspection ("NI") for the entire F-15C aircraft fleet is scheduled to occur thereafter in sixty months pursuant to treatment plan ALC-M890538-00.

Treatment plans ALC-I99061-02, ALC-R890444-01, ALC-RR890526-01, and ALC-M890538-00 consist of digital code-driven tables. Such tables typically consist of airplane repair station procedures and processes necessary for inspection, maintenance, and repair. Furthermore, such tables may also contain digital sub-tables of required and interrelated repair station resources. Examples of interrelated repair station resources include, but are not limited to, facilities, equipment, manpower, man-hours, service-time, and direct and indirect costs and the utilization sequence of same in the inspection, maintenance, and repair process. By way of example, a table-driven procedure for ALC-RR890526-01, which may be automatically selected when implementing Boolean logic rules, includes: (a) identifying repair procedures and/or develop new or additional procedures; (b) identifying direct and indirect materials needed for repair; (c) identifying any special tooling and equipment needed for the repair; (d) identifying or determine mechanic, technician, and specialist repair team certifications and training needs to satisfy repair procedures; (e) scheduling prototype development on repair procedures; (f) identifying or develop technical data for the processes; (g) identifying amount of spares available in supply; (h) inspecting spares as in Example 1A for defects; (i) repairing deficient spares in preparation as a replacement part; (j) Re-inspecting all repaired spares for proper repair; (k) identifying or determine repair timeline for scheduling of resources; (l) scheduling facility, equipment, inventory, materials, and human resources required; (m) scheduling airplane fleet for induction into repair at repair station; (n) projecting repair budget; (o) inducting the airplane fleet for horizontal stabilizer repair; (p) repairing dismantled left or right horizontal stabilizer; (q) inspecting repaired left or right horizontal stabilizer for defects before placing it into spares inventory.

Figure 23A:
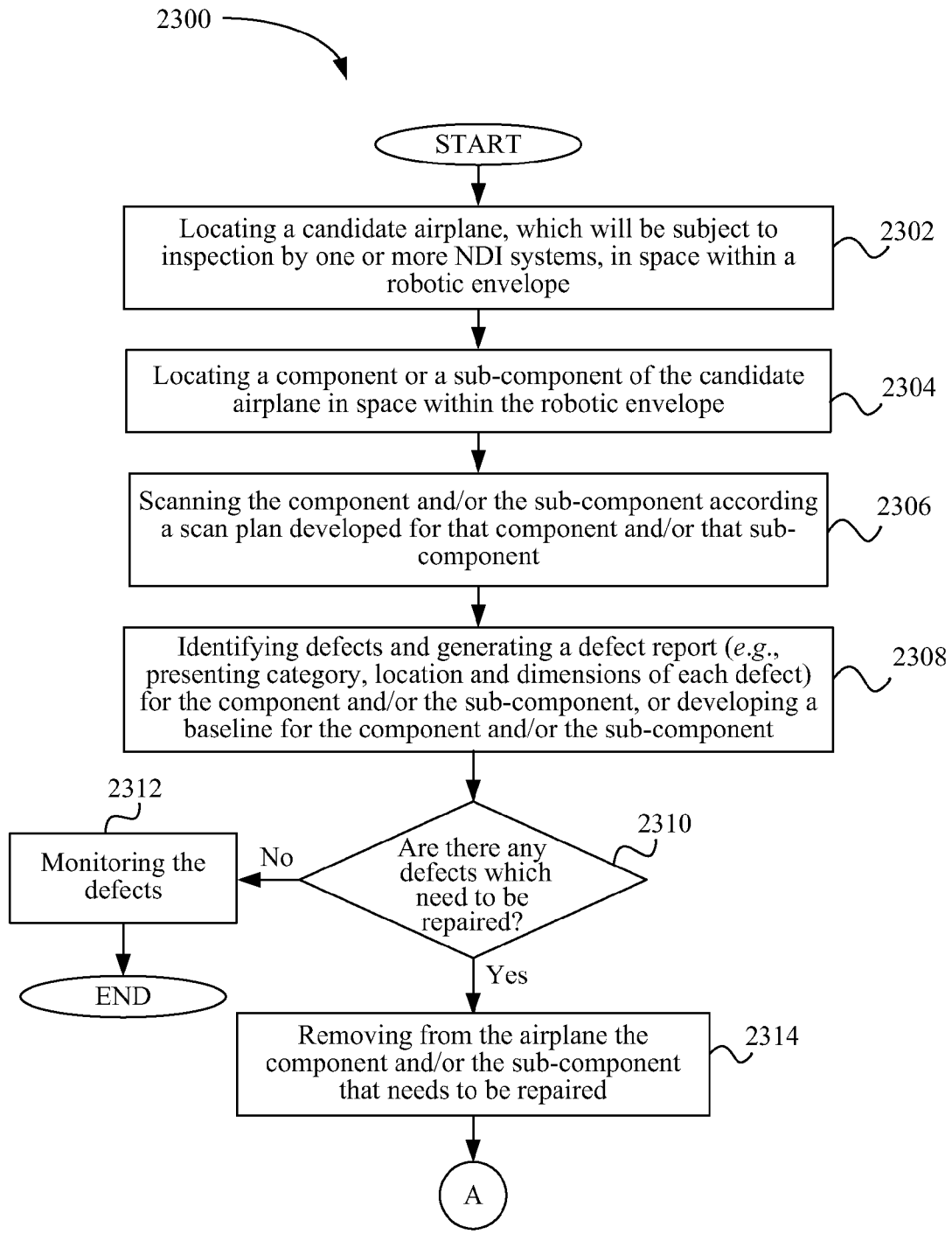
FIGS. 23A and 23B shows a process flow diagram, in accordance with preferred embodiments of the present invention, for managing or repairing defects found in an airplane's component or sub-component using an NDI system and when the repair requires removing the defective component or sub-component from the airplane.

FIG. 23A shows a process 2300, according to a preferred embodiment of the present invention, for airplane inspection which requires removal of a defective component or sub-component. In this embodiment, inventive process 2300 begins with a step 2302. Step 2302 includes locating a candidate airplane, which will be subject to inspection by one or more NDI systems, in space within a robotic envelope. Next, a step 2304 includes locating a component or a sub-component of the candidate airplane in space within the robotic envelope.

Once the airplane and the component or the sub-component is located in space, one or more NDI systems are in position to commence a scanning step. A step 2306 includes scanning the component or the sub-component according to a scan plan developed for that component or that sub-component. As mentioned above, each robot associated with an NDI system is taught a scan plan (e.g., step 1506 of FIG. 15) during a previous process of forming a gold body database.

A step 2308 includes identifying defects to generate a defect report (e.g., presenting category, location and dimensions of each defect) for the component or the sub-component, and/or to develop a baseline for the component or the sub-component. In a following step 2310 it is inquired whether there are any defects which need to be repaired. As mentioned before, defects are preferably evaluated against a predetermined accept/reject criteria to determine corrective maintenance and repair actions If it is determined that none of the defects identified need to be repaired, then process 2300 moves to a step 2312, which includes monitoring the defects over a period of time when inspections such as the ones described above are carried out. Monitoring includes tracking defects growth in length, width and depth.

If, however, it is determined that one or more defects need to be repaired, then process 2300 moves to a step 2314, which includes removing from the airplane the component or the sub-component that needs to be repaired. After step 2314, various steps involved in process 2300 are presented in FIG. 23B.

Figure 23B:
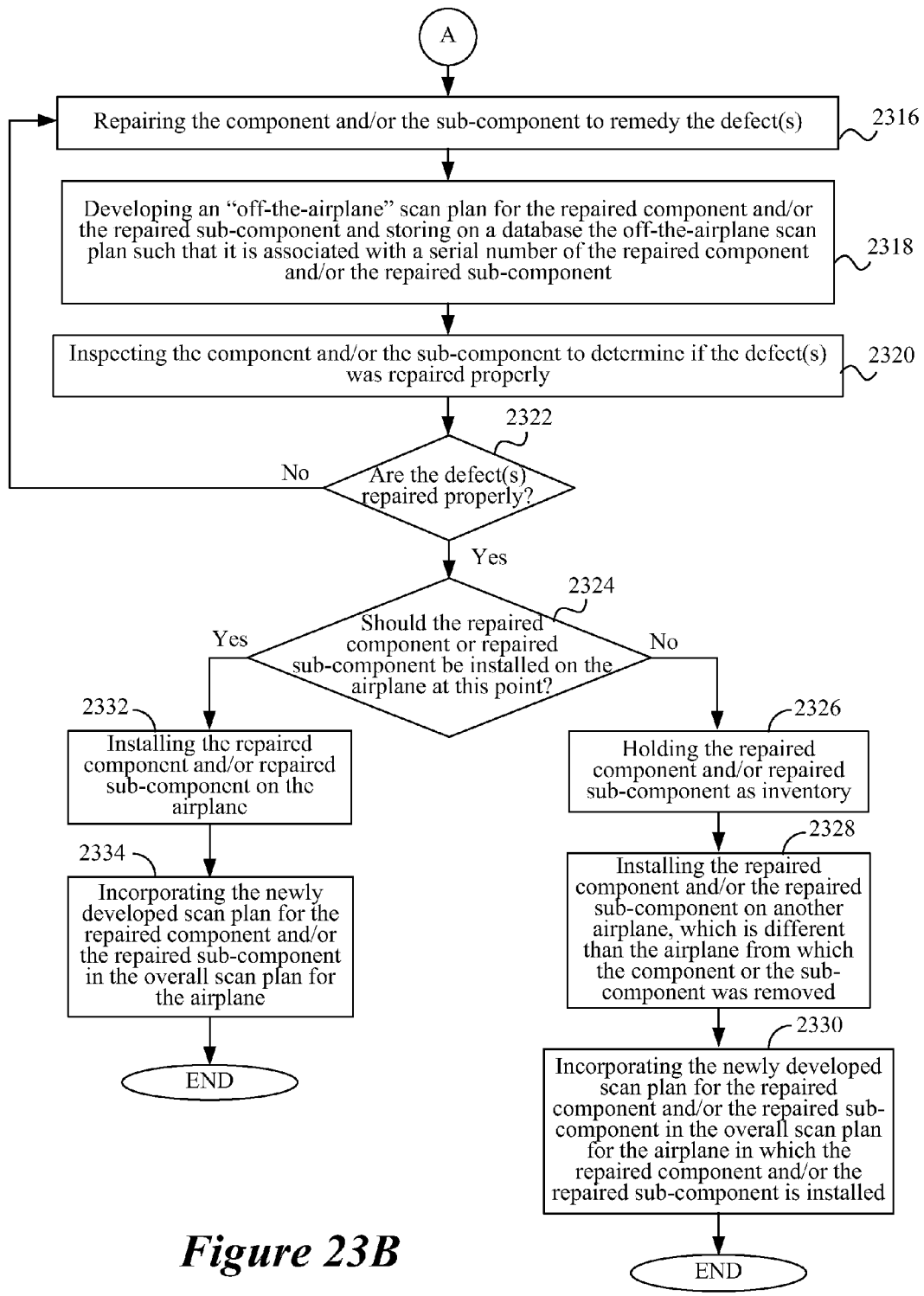

According to FIG. 23B, a step 2316 follows step 2314 (of FIG. 23A) and includes repairing the component or the sub-component to remedy the defect(s). Next, a step 2318 includes developing an "off-the-airplane" scan pan for the repaired component or the repaired sub-component and storing on a database the off-the-airplane scan plan such that it is associated with a serial number of the repaired component or the repaired sub-component. An "off-the-airplane" scan plan looks similar to the scan plans shown in FIGS. 17 and 18. However, as the name suggests, an "off-the-airplane" scan plan is developed when a component or a sub-component is off the airplane. Then, a step 2320 is carried out and includes inspecting the component or the sub-component to determine if the defect was repaired properly.

A step 2322 inquires whether the defect was repaired properly. If it is determined that the defect was not repaired properly, then process 2300 goes back to step 2316, where repairs are carried out again. Steps 2318, 2320 and 2322 follow the repair step of 2316. In this manner, steps 2316, 2318, 2320 and 2322 may be carried out, according to a loop shown in FIG. 23B, until the defects are repaired properly.

If, however, it is determined that the defect was repaired properly, then process 2300 moves forward to a step 2324, where another inquiry is made. In step 2324, it is inquired whether the properly repaired component or the properly repaired sub-component should be installed on the airplane at this point. In other words, step 2324 inquires whether another component or sub-component should be installed on the candidate airplane, instead of installing the repaired component or the repaired sub-component. Such an inquiry may be made for a variety of reasons. By way of example, if the repair process is long and time-consuming, another component or sub-component from inventory is installed on the candidate airplane so that the candidate airplane is back to being functional in short order.

If it is determined in step 2324 that that the repaired component or sub-component should be installed at that point on the candidate airplane, then process 2300 moves to a step 2332, which requires installing the repaired component or repaired sub-component on the airplane. Next, in a step 2334 the newly developed scan plan for the repaired component or the repaired sub-component is incorporated into the overall scan plan for the airplane. In preferred embodiments of the present invention, step 2334 is carried out by assigning a scan plan developed for the repaired component or repaired sub-component to the tail number of a candidate airplane.

If it is determined in step 2324 that that the repaired component or sub-component should not be installed at that point on the candidate airplane, then process 2300 moves to a step 2326, which requires holding the repaired component or the repaired sub-component as inventory. Next, in a step 2328 the repaired component or the repaired sub-component is installed on another airplane, which is different than the airplane from which the component or the sub-component was removed, as mentioned in step 2314 of FIG. 23A.

A step 2330 includes incorporating the newly developed scan plan for the repaired component or the repaired sub-component in the overall scan plan for the airplane in which the repaired component or the repaired sub-component is installed. As a result, for subsequent inspection of the airplane, there exists an updated gold body database to effectively identify defects.

Figure 24A:
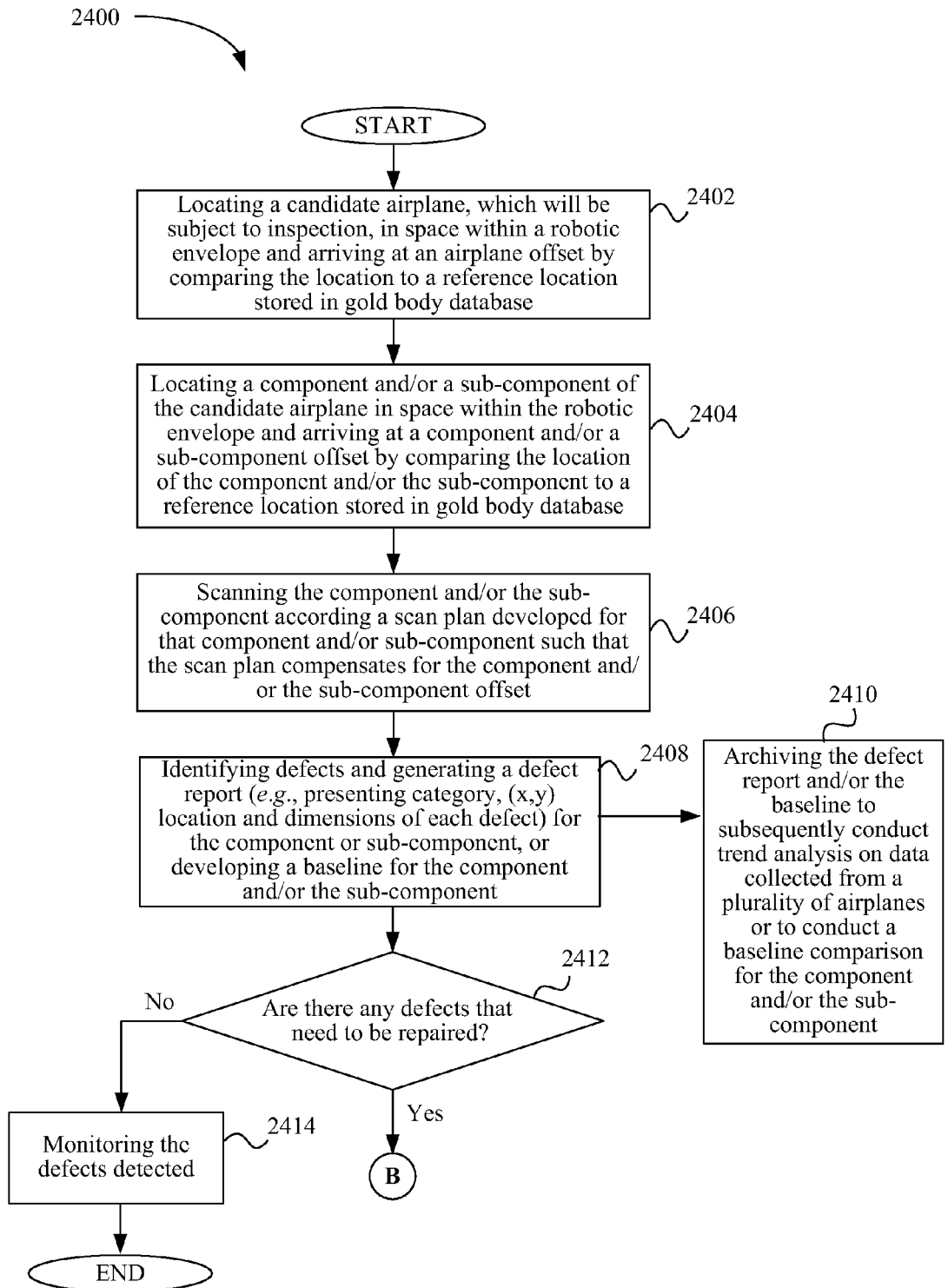
FIGS. 24A and 24B shows a process flow diagram, in accordance with preferred embodiments of the present invention, for managing or repairing defects found in an airplane's component or sub-component using an NDI system and when the repair is carried out on an intact airplane (i.e., the defective component or sub-component is not removed from the airplane).
Figure 24B:
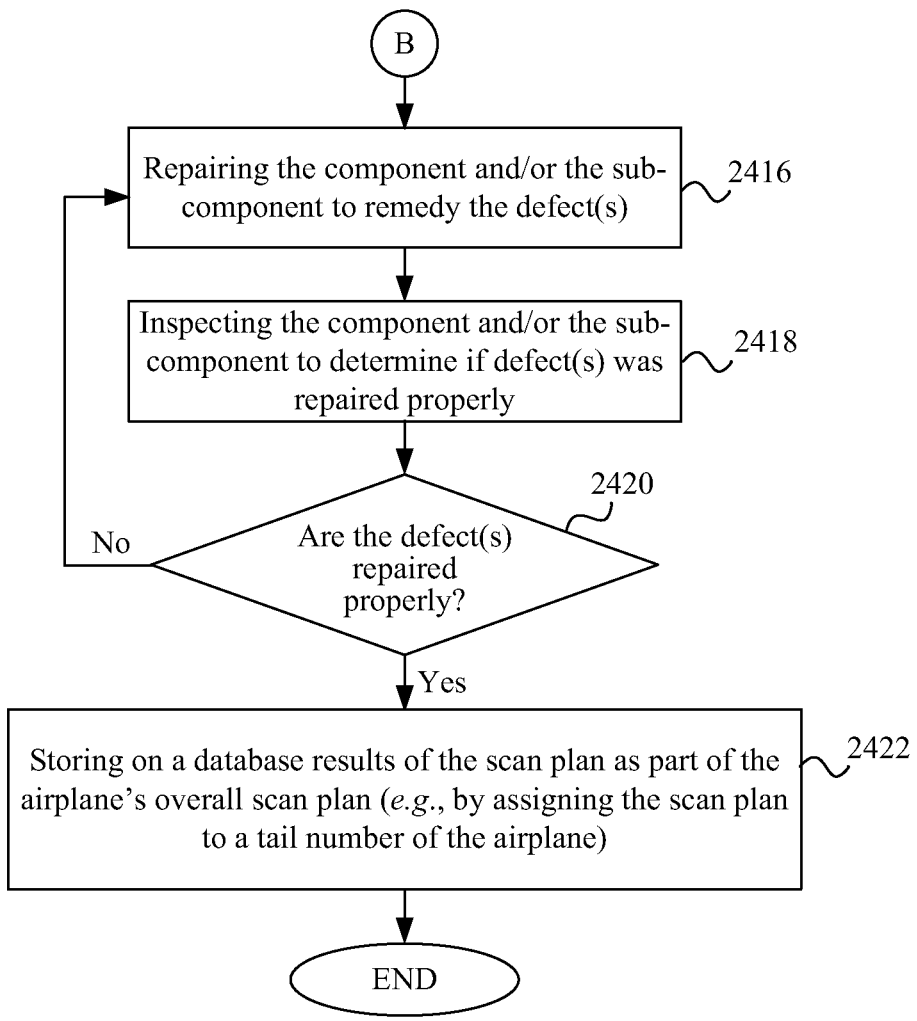

FIG. 24A shows a process flow diagram for a process 2400, according to one preferred embodiment of the present invention, for an airplane inspection, which does not require removal of a defective component or sub-component. Process 2400 preferably begins with a step 2402 which includes locating a candidate airplane, which will be subject to inspection by one or more NDI systems, in space within a robotic envelope. In step 2402, an airplane offset is arrived at by comparing a current location of the airplane to a reference location of the airplane. The reference airplane location is preferably stored as part of the airplane's gold body database. The offset preferably represents a difference between a current location of the airplane to the reference location of the airplane.

Next, a step 2404 includes locating a component or a sub-component of the candidate airplane in space within the robotic envelope. Like step 2402, step 2404 also arrives at an offset. However, in step 2404 the offset may be called a "component offset" or a "sub-component offset," as it results from the comparison between the current location of the component or the sub-component and the reference location of the component or the sub-component stored in the gold body database.

A step 2406 is then carried out to scan the component or the sub-component according to a scan plan developed for that component or that sub-component, such that the scan plan compensates for the component offset or the sub-component offset. In other words, the scan plan is initiated when the reference points (i.e., the zero-zero coordinates) of the component or the sub-components located in space are established from the component or the sub-component offsets.

Next, a step 2408 includes identifying defects to generate a defect report (e.g., presenting category, location and dimensions of each defect) for the component or the sub-component, and/or to develop a baseline for the component or the sub-component. The defect report and/or baseline obtained from step 2408 is archived in step 2410 so that at a later time, it is possible to conduct a trend analysis on data collected from a plurality of airplanes, or conduct a base line comparison for the component or the sub-component. After step 2408, it is inquired whether there are any defects which need to be repaired.

If it is determined that none of the defects identified need to be repaired, then process 2400 moves to a step 2414, which includes monitoring the defects over a period of time when inspections such as the ones described above are carried out.

If, however, it is determined that one or more defects need to be repaired, then process 2400 moves to a step 2416 (shown in FIG. 24B), which includes repairing the component or the sub-component to remedy the defect(s). Next, a step 2418 is carried out and includes inspecting the component or the sub-component to determine if the defect was repaired properly.

A step 2420 inquires whether the defect was repaired properly. If it is determined that the defect was not repaired properly, then process 2300 goes back to step 2416, where repairs are carried out again. Steps 2418 and 2420 follow the repair step of 2416. In this manner, steps 2416, 2418 and 232 may be carried out, according to a loop shown in FIG. 24B, until the defect(s) are repaired properly.

If, however, it is determined that the defect was repaired properly, then process 2400 may conclude at a step 2422 which includes storing on a database results of the scan plan of the airplane's overall scan plan. In preferred embodiments of the present invention, step 2422 is carried out by assigning the scan plan to a tail number of the airplane.

In certain embodiment of the present invention, once a repaired component passes post inspection (i.e., the inquiry in steps 2322 (of FIG. 23) and 2420 (of FIG. 24) are answered in the affirmative), archival data and images are assigned and recorded to that specific component by the component's part and serial numbers, and by the tail number of the airplane on which it is installed. Cradle to grave identification of all inspected components, by intact airplane systems or component systems, are archived and indexed by tail number, part number and serial number. Spare parts are inspected prior to installation and eventually identified and indexed to specific airplane tail number.

It is noteworthy that candidate airplanes, undergoing inspection, are not absolutely required to be jacked in place for stabilization. In such instances, the airplane may be located within the robotic envelope to the line markings on the floor plus or minus eight inches. The robot then seeks to locate the vision edges on the airplane. Once located, the robot automatically recognizes where the taught airplane was in reference and where follow-on production airplane is located. As explained above, this is called an offset and is transparent to system operators. Scan plan accuracy is preferably about 0.120 thousands of an inch on all production airplanes. Given that no two airplanes are exactly the same, a system operator can manually align the robot by joystick control to the beginning zero-zero coordinates on each and every component or sub-component, allowing about 0.120 thousands of accuracy of scan for each component or each sub-component from airplane to airplane. For precise measurement and evaluation of defects, manual alignment can also be accomplished by aligning to a particular defect.

This description of the disclosed aspects of the present invention is provided to enable any person skilled in the art to make or use the present invention. Various modifications to these aspects will be readily apparent to those skilled in the art, and the generic principles defined herein may be applied to other aspects without departing from the spirit or scope of the invention. Moreover, having thus described the invention, it should be apparent that numerous structural modifications and adaptations may be resorted to without departing from the scope and fair meaning of various embodiments of the instant invention as set forth hereinabove and as described herein below by the claims.

What is claimed is:

1. A system for developing a gold body database for a particular non-destructive inspection method, said system comprising:

means for teaching within a robotic envelope a robot, which is used in said particular non-destructive inspection method, at least two edges defining a boundary of a reference airplane;

means for teaching said robot at least two edges defining a boundary of a component or a sub-component of said reference airplane in space within a robotic envelope, such that during a subsequent inspection of a plurality of candidate airplanes of said particular model for presence of defects, a corresponding component or sub-component in each of plurality of said candidate airplanes is automatically located in space using said robot; and means for teaching a scan plan for said component or said sub-component located in space for each non-destructive inspection system subsequently implemented to detect defects in each of plurality of said candidate airplanes.

2. The system of claim 1, wherein said means for locating a-said reference airplane and said means for locating said component or said sub-component in space include a machine vision system associated with each non-destructive inspection system implemented.

3. The system of claim 1, wherein said means for said scan plan includes means for teaching an electromagnetic radiation emitter and a detector, both of which are configured to a yoke to provide rotation about at least one axis of pitch, rotate and yaw motion of said at least one of said electromagnetic radiation emitter and said detector, said yoke includes a first and a second members, said first member supports said electromagnetic radiation emitter and said second member supports said detector such that a distance between said electromagnetic radiation emitter and said detector is adjustable.

4. A method of developing a gold body database for a particular non-destructive inspection method, said method of developing a gold body database comprises:

teaching within a robotic envelope a robot, which is used in said particular non-destructive inspection method, at least two edges defining a boundary of a reference airplane;

teaching said robot, using machine vision, at least two edges defining a boundary of a component or a sub-component of said reference airplane in space within said robotic envelope, such that during a subsequent inspection of a plurality of candidate airplanes of said particular model for presence of defects, a corresponding component or sub-component in each of plurality of said candidate airplanes is automatically located in space using said robot; and teaching a scan plan for said component or said sub-component located in space for each non-destructive inspection system subsequently implemented to detect defects in each of plurality of said candidate airplanes.

5. The method of claim 4, further comprising storing on a database said scan plan for said component or sub-component, and said scan plan is part of said gold body database.

6. The method of claim 4, wherein said teaching said robot, which is used in said particular non-destructive inspection method, edges that define said boundary of said reference airplane includes:

aligning a nose gear or a main landing gear tire to a center line and a line on a floor of said robotic envelope, respectively;

immobilizing said reference airplane;

taking load off tires or actuators of said reference airplane;

defining point to point movement of said robot to approach said reference airplane such that said robot does not collide with an external object or said reference airplane; and wherein said teaching a robot, using machine vision, at least two edges defining a boundary of said reference airplane is carried out such that during said subsequent inspection of said plurality of candidate airplanes, each of said plurality of candidate airplanes is automatically located in space using said robot.

7. The method of claim 6, wherein teaching said robot, using machine vision, at least two edges defining a boundary of said component or said sub-component of said reference airplane in space includes:

teaching said robot registration points on said component or said sub-component that define a shape of said component or said sub-component located in space; and establishing a zero-zero coordinate in x-y plane for said component or said sub-component such that said scan plan determined for each non-destructive inspection system and for said component or said sub-component is implemented during said subsequent inspection of said plurality of candidate airplanes.

8. The method of claim 7, further comprising for each non-destructive inspection method:

establishing a value for location of said component or said subcomponent in z-axis; and implementing pitch, rotate and yaw for proper alignment to internal structures.

9. The method of claim 4, wherein said teaching a scan plan includes programming said robot to follow a specific raster scan path depending on the non-destructive inspection system.

* * * * *